United States Patent [19]

London et al.

[11] Patent Number: 5,639,906
[45] Date of Patent: Jun. 17, 1997

[54] FLUORESCENT AND NMR SENSITIVE PH INDICATORS

[75] Inventors: Robert E. London; Louis A. Levy, both of Chapel Hill; Chung K. Rhee, Durham, all of N.C.

[73] Assignee: The United States of America as represented by the Department of Health and Human Services, Washington, D.C.

[21] Appl. No.: 320,986

[22] Filed: Oct. 11, 1994

[51] Int. Cl.⁶ .................. C07C 69/76; C07C 229/00; C07C 211/00
[52] U.S. Cl. .................. 560/62; 562/452; 564/207; 564/366
[58] Field of Search .................. 562/452; 560/62; 564/366, 207

[56] References Cited

FOREIGN PATENT DOCUMENTS 9321162  10/1993  WIPO.

OTHER PUBLICATIONS

Costales, et al., ACS Symp. Ser. 504(Synth. Chem. Agrochem. III), 26–33 *Abstract* 1992.
Beech et al., "$^{19}$F n.m.r. indicators of hepatic intracellular pH in vivo," *Biochem. Soc. Trans.* 15:871–872 (1987).
Cobbold et al., "Fluorescence and bioluminescence measurement of cytoplasmic free calcium," *Biochem. J.* 248:313–328 (1987).
DeFronzo et al., "Characterization of methylphosphonate as a $^{31}$P NMR pH indicator," *J. Biol. Chem.* 262:11032–11037 (1987).
Deutsch et al., "Regulation of intracellular pH by human peripheral blood lymphocytes as measured by $^{19}$F NMR," *PNAS USA* 79:7944:7948 (1982).
Deutsch et al., "Intracellular pH as measured by $^{19}$F NMR," *Physiological NMR Spectroscopy: From Isolated Cells to Man,* Ann. N.Y. Acad. Sci. 508:33–47 (1987).
Deutsch et al., "$^{19}$F NMR measurements of intracellular pH," Chapter 10, vol. II, pp. 55–74, *NMR Spec. of Cells & Organisms 1987.*
Deutsch et al., "New class of $^{19}$F pH indicators: fluoroanilines," *Biophys. J.* 55:799–804 (1989).
Evelhoch et al., "In vivo metabolic effects of hyperglycemia in murine radiation–induced fibrosarcoma: A $^{31}$P NMR investigation," *PNAS USA* 81:6496–6500 (1984).
Grynkiewicz et al., "A new generation of $Ca^{2+}$ indicators with greatly improved fluorescence properties," *J. Biol. Chem.* 260:3440–3450 (1985).
Haugland, R., "Set 21: pH Indicators," *Molecular Probes: Handbook of Fluorescent Probes and Research Chemicals (5th Ed., 1992–1994),* pp. 129–141 (ed. Karen D. Larison, Eugene, OR).
Jacobson et al., "Intracellular pH Measurements by NMR Methods" In: *Noninvasive Probes of Tissue Metabolism,* pp. 5–25 (ed. J.S. Cohen, Wiley, NY (1982)).

Levy et al., "Measurement of cytosolic free magnesium ion concentration by $^{19}$F NMR," *Biochemistry* 27:4041–4048 (1988).
Lewis et al., "Muscle fatigue in McArdle's disease studied by $^{31}$P–NMR: effect of glucose infusion," *J. Appl. Physiol.* 59:1991–1994 (1985).
London et al., "Determination of membrane potential and cell volume by $^{19}$F NMR using trifluoroacetate and trifluoroacetamide probes," *Biochemistry* 28:2378–2382 (1989).
London, "Chemical–shift and linewidth characteristics of reversibly bound ligands," *J. Magn. Reson. Series A* 104:190–196 (1993).
Mehta et al., "Fluorinated macromolecular probes for non-invasive assessment of pH by magnetic resonance spectroscopy," *Biorganic & Med. Chem. Letters,* 3:187–192 (1993).
Mehta et al., "6–fluoropryidoxol: a novel probe of cellular pH using $^{19}$F NMR spectroscopy," *FEBS Letters* 349:234–238 (1994).
Metcalfe et al., "Free cytosolic $Ca^{2+}$ measurements with fluorine labelled indicators using $^{19}$FNMR," *Cell Calcium* 6:183–195 (1985).
Minta et al., "Fluorescent indicators for cytosolic calcium based on rhodamine and fluorescein chromophores," *J. Biol. Chem.* 264:8171–8178 (1989).
Moon et al., "Determination of intracellular pH by $^{31}$P magnetic resonance," *J. Biol. Chem.* 248:7276–7278 (1973).
Raju et al., "A fluorescent indicator for measuring cytosolic free magnesium," *Am. J. Physiol.* 256:C540–C548 (1989).
Rink et al., "Cytoplasmic pH and free $Mg^{2+}$ in lymphocytes," *J. Cell Biol.* 95:189–196 (1982).
Roberts et al., "Intracellular pH measurements by $^{31}$P nuclear magnetic resonance. Influence of factors other than pH on $^{31}$P chemical shifts," *Biochemistry* 20:5389–5394 (1981).
Ross et al., "Examination of a case of suspected McCardle's syndrome by $^{31}$P nuclear magnetic resonance," *N. Engl. J. Med.* 304:1338–1342 (1981).
Smith et al. "A new $^{19}$F NMR indicator for intracellular sodium," *J. Chem. Soc. Perkin Trans.* 2:1205–1209 (1993).
Szwergold et al., "Bicarbonate abolishes intracellular alkalinization in mitogen–stimulated 3T3 cells" *J. Cell. Physiol.* 138:227–235 (1989).

(List continued on next page.)

*Primary Examiner*—Joseph Conrad
*Attorney, Agent, or Firm*—Townsend and Townsend and Crew LLP

[57] ABSTRACT

This invention relates to compositions and methods useful for measuring pH generally, and intracellular pH specifically, and, more particularly, to a new class of fluorescent and fluorinated (NMR sensitive) aromatic compounds having excitation emission wavelengths in the ultraviolet or or visible portions of the electromagnetic spectrum, useful as pH indicators, as well as fluorine containing analogs useful in NMR spectroscopic determinations.

7 Claims, 3 Drawing Sheets

OTHER PUBLICATIONS

Taylor et al., "Measurement of transmembrane pH gradients in human erythrocytes using $^{19}$F NMR," *Analytical Biochemistry* 114:415–418 (1981).

Taylor et al., "Fluorinated α-methlyamino acids as $^{19}$F NMR indicators of intracellular pH," *Biophys. J.* 43:261–267 (1983).

Thoma et al., "pH measurements by $^{31}$p NMR in bacterial suspensions using phenyl phosphonate as a probe," *Biochem. Biophys. Res. Commun.* 138:1106–1109 (1986).

Tsien et al., "T–cell mitogens cause early changes in cytoplasmic free $Ca^{2+}$ and membrane potential in lymphocytes," *Nature* 295:68–71 (1982).

Tsien et al., "Calcium homeostasis in intact lymphocytes: cytoplasmic free calcium monitored with a new, intracellularly trapped fluorescent indicator," *J. Cell Biol.* 94:325:334 (1982).

Tsien et al., "Measurement of cytosolic free $Ca^{2+}$ in individual small cells using fluorescence microscopy with dual excitation wavelengths," *Cell Calcium* 6:145–157 (1985).

FLUORESCENT AND NMR SENSITIVE PH INDICATORS

FIELD OF THE INVENTION

This invention relates to compositions and methods useful for measuring pH generally, and intracellular pH specifically, and, more particularly, to a new class of fluorescent and fluorinated (NMR sensitive) aromatic compounds having excitation emission wavelengths in the ultraviolet or or visible portions of the electromagnetic spectrum, useful as pH indicators, as well as fluorine containing analogs useful NMR spectroscopic determinations.

BACKGROUND OF THE INVENTION

Intracellular pH is an important regulator of a broad range of metabolic and physiological processes, and plays a central role in cell function, growth and development (See, e.g., *Intracellular pH: Its Measurement, Regulation and Utilization in Cellular Functions*, Liss, New York, 1982). The pH gradient between the mitochondrion and the cytosol is believed to play a critical role in mitochondrial function, and hence in cellular energy production (Mitchell, *Science* 206, 1148–1149; 1979).

Disturbances in cellular pH regulation occur with many pathological conditions, and have sometimes been used diagnostically. The first successful use of in vivo NMR spectroscopy to diagnose human disease, a case of McArdle's syndrome, was based on a measurement of intracellular pH and its response to exercise (Ross et al., *N. Engl. J. Med.* 304, 1338–1342; 1981; Lewis et al., *J. Appl. Physiol.* 59, 1991–1994; 1985). It has often been observed that the intracellular pH or the pH regulation of carcinogenically transformed cells differs significantly from that of non-transformed cells. For example, dramatic intracellular acidification in response to hyperglycemia has been observed in murine RIF-1 tumors (Evelhoch et al., *PNAS USA* 81: 6496–6500; 1984). It has been proposed that the relationship between malignancy and pH is due in part to increased acidic glycolysis in conjunction with a decreased or absent Pasteur effect—the so-called "Warburg effect" (see, e.g., Goldberg, et al., *Clin. Chem.* 39,2360–2374; 1993; Weinhouse, et al., *Krebsforsch.* 87, 115–126; 1976). Also, the inner cells of solid tumors often become hypoxic as a result of reduced blood flow, and therefore are subject to acidification due to increased glycolytic flux. Hence, the ability to determine pH in cells and organisms is of fundamental significance in a broad range of biological processes, and is useful for analyzing and diagnosing many pathological conditions.

The traditional methods for determining intracellular pH include microelectrode techniques, studies of the distribution of weak acids and bases, and analyses based on extracted metabolites (Cohen and R. A. Iles, *CRC Critical Revs. in Clinical and Lab. Sci.* 6, 101–143; 1975). Although microelectrode technology has improved considerably, thereby extending the range of such measurements to individual cells, these methods are cumbersome and subject to large errors. The introduction of fluorescent microscopy combined with fluorescent pH indicators, and in vivo NMR techniques, has widened the availability of such measurements to perfused organs, experimental animals, and humans.

Typical NMR methods of pH determination utilize endogenous phosphorylated molecules whose chemical shift is pH dependent (Cohen, et al., in *Critical Revs. in Clin. Lab. Sciences* 6, 101; 1975; Jacobson, L.; Cohen, J. S. "Intracellular pH Measurements by NMR Methods" In: *Noninvasive Probes of Tissue Metabolism*. Cohen, J. S., Ed. Wiley: New York, 1982; Moon, R. B.; Richards, J. H. *J. Biol. Chem.* 248, 7276–7278; 1973; Roberts, J. K. M.; Wade-Jardetzky, N.; Jardetzky, O. *Biochemistry* 20, 5389; 1981); however, this approach is limited by several factors including the low concentration of inorganic phosphate (the most useful pH indicator) in many cells, significant interference from extracellular phosphate present in blood, buffers, or perfusates, the overlap of the phosphate resonance with resonances from various phosphomonoesters, and the absence in some cell types of a suitable metabolite to serve as a chemical shift reference. Consequently, exogenous NMR probes of intracellular pH have been described and developed in the art. (Thoma, J. W.; Steiert, J. G., Crawford, R. L., Ugurbil, K. *Biochem. Bioshys. Res. Commun.* 1986, 138, 1106; DeFronzo, M.; Gillies, R. J. *J. Biol. Chem.* 262, 11032 (1987); Szwergold, B. S.; Brown, T. R.; Freed, J. *J. Cell. Physiol.* 138, 227 (1989); Taylor, J. S.; Deutsch, C. J.; McDonald, G. G.; Wilson, D. F. *Anal. Biochem.* 114, 415 (1981); Taylor, J. S.; Deutsch, C. J. *Biophys. J.* 43, 261 (1983); Deutsch, C. J.; Taylor, J. S. *Ann. N.Y. Acad. Sci.* 508, 33 (1987); Deutsch, C. J.; Taylor, J. S. *Bioshys J.* 55, 799 (1989); Metcalfs, J. C.; Hesketh, T. R.; Smith, G. A. *Cell Calcium* 6, 188 (1985); Beech, J. S.; Iles, R. A. *Biochem. Soc. Trans.* 15, 871 (1987)).

In principle, exogenous NMR probes can be optimized for pH measurement based on criteria including: (1) resonances should exhibit a large change in chemical shift with change in pH ($\Delta\delta/\Delta pH$) and a pK close to the physiological mean; (2) high detection sensitivity; (3) indicators should be capable of being loaded into cells and should not readily leak out once they are loaded; (4) there should be minimal overlap between the resonances of the indicator and those of other endogenous metabolites; and (5) if the chemical shift is the parameter of interest, the indicator should contain an internal reference so that no additional reference is required. Based on the above criteria, the use of fluorinated indicators is particularly attractive since criteria (2) and (4) can be completely satisfied, and, due to the high chemical shift sensitivity of $^{19}F$, the first criterion can be satisfied as well with an appropriate design of the indicator.

Similarly, exogenous fluorescent probes for intracellular pH designed for optimal pH determination would have: (1) a pK close to the level being monitored; (2) a quantum yield and fluorescence intensity sufficiently high so that cellular autofluorescence does not interfere with the measurement; (3) a fluorescence spectrum which exhibits minimal overlap with the natural autofluorescence spectrum of the cell; (4) a shift in the fluorescence excitation and/or emission maximum upon titration so that dual wavelength measurement and imaging techniques can be used; (5) sufficient charge to reduce interaction with hydrophobic binding sites in the cell and to lead to negligible leakage on the time scale of the measurements; and (6) a structure which is not readily subject to metabolic transformation in the cell, other than de-esterification used for loading.

One useful fluorescent indicator for intracellular pH is the molecule bis(carboxyethyl)carboxyfluorescein (BCECF) (Rink et al., *J. Cell Biol.* 95: 189–196; 1982). Other commercially available indicators are described, for example, in Haugland, R. P.; Larison, K. D., *Handbook of Fluorescent Probes and Research Chemicals*, 5th ed. (1992–1994) Eugene Oreg., pp. 129–142. In general, the available fluorescent intracellular pH probes fail to adequately meet the above criteria; in particular, they suffer from pK values which are not well matched to the cytosol, they tend to leak significantly, and they tend to bind with hydrophobic sites on intracellular consitutents such as cellular proteins.

SUMMARY OF THE INVENTION

The present invention includes a new class of fluorescent intracellular pH indicators having excitation and emission wavelengths in the ultraviolet or visible portions of the electromagnetic spectrum, as well as fluorine-containing analogs which are useful for $^{19}F$ NMR spectroscopic determinations. The chromophoric or fluorescent indicators of this invention are based on a central N-alkyl-2-aminophenol structure. More specifically, by utilizing an N-alkyl-2-aminophenol structure, chromophoric properties can be constructed which have pK values in a physiologically useful range. Additionally, these indicators have a reduced affinity for cellular cations so that binding of alkali or alkali earth ions does not interfere with pH determination. Quantitation of pH values is achieved by monitoring changes in the spectral properties of these indicators. These indicators are particularly useful in the determination of intracellular or intra-organelle pH.

In another embodiment, the present invention includes fluorinated analogs of these indicators with the fluorine nucleus located in the aniline ring, most typically in the para position relative to the amino group. The fluorine exhibits a chemical shift which is sensitive to the protonation state of the amino group. Some embodiments utilize a second fluorine nucleus which then serves as an internal chemical shift reference for the pH sensitive peak. Since the change in chemical shift of a p-fluoroaniline due to titration of the amino group is typically large, ~11 ppm, the method is sensitive to small pH variations, and can also be used to monitor the pH from cellular compartments into which the indicator is loaded.

One embodiment of the invention includes compounds, and salts thereof, which are represented by the Formula I:

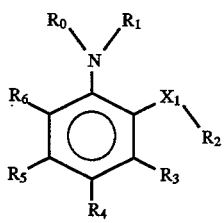

Formula I $R_0$–$R_2$ are selected independently from the group consisting of hydrogen, alkyl, aryl, substituted alkyl, substituted aryl, carboxyl, carboxyalkyl, substituted carboxyalkyl, heteroaryl and substituted heteroaryl. $R_3$–$R_6$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $X_1$ is selected from the group consisting of oxygen, nitrogen, and sulfur.

However, (a) $R_0$, $R_1$ and $R_2$ are not all —$CH_2CO_2H$ or —$CH_2CO_2CH_3$ when $X_1$ is oxygen, $R_4$ is fluorine or hydrogen, $R_5$ is hydrogen, fluorine or methyl, and $R_3$ and $R_6$ are hydrogen; (b) $R_0$ and $R_1$ are not both —$CH_2CO_2H$ when $X_1$ is oxygen, $R_4$ is fluorine and $R_3$, $R_5$ and $R_6$ are hydrogen, and $R_2$ is —$(CH_2)_2O(CH_2)_2N(CH_2CO_2H)_2$; (c) $R_0$ and $R_1$ are not both —$CH_2CO_2H$ when $X_1$ is oxygen, $R_3$, $R_4$, $R_5$ and $R_6$ are fluorine or hydrogen, and $R_2$ is —$(CH_2)_2O(C_6H_3N(CH_2CO_2H)_2F)$; (d) $R_0$ and $R_1$ are not both —$CH_2CO_2H$ or —$CH_2CO_2CH_3$ when $X_1$ is oxygen, $R_4$ is fluorine, $R_5$ is methyl, —$C(CH_3)_2CH_2CO_2H$ or —$C(CH_3)_2CH_2CO_2CH_3$, and $R_3$ and $R_6$ are hydrogen; (e) $R_0$ and $R_1$ are not both —$CH_2CO_2H$ or —$CH_2CO_2CH_3$ when $X_1$ is oxygen, $R_4$ is fluorine, $R_5$ and $R_6$ are hydrogen, and $R_2$ is an (8-amino-2-quinoline)methyl; (f) $R_0$ and $R_1$ are not both —$CH_2CO_2CH_2C_6H_5$ when $X_1$ is oxygen, $R_4$ is fluorine, $R_3$, $R_5$ and $R_6$ are hydrogen, and $R_2$ is —$(CH_2)_2O(CH_2)_2N(CH_2CO_2CH_2C_6H_5)_2$; (g) $R_0$ is not —$C(CH_3)_2CO_2CH_3$ or —$C(CH_3)_2CO_2H$ when $R_1$ is hydrogen or methyl, $X_1$ is oxygen, $R_4$ is fluorine, and $R_3$, $R_5$ and $R_6$ are hydrogen; and (h) at least one of $R_3$–$R_6$ is fluorine.

A representative embodiment of these indicators is the compound N-carboxymethyl-N,O-dialkyl-2-amino-5-fluorophenol (hereinbelow abbreviated "NAAP"):

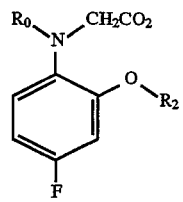

where $R_0$ and $R_2$ are alkyl or substituted alkyl groups. A specific representative embodiment of these indicators is the analog to the NAAP compound, N-ethyl-2-aminophenol-N, O-diacetate (hereinbelow abbreviated "NEAP"), where $R_0$ is ethyl and $R_2$ is carboxymethyl:

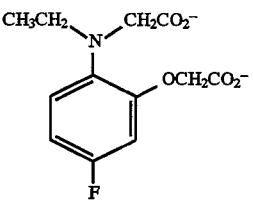

This molecule has a pK of 6.8 and the fluorine-19 resonance of the para-fluorine nucleus undergoes a downfield shift of about 11 ppm upon protonation of the nitrogen substituent.

Alternatively, $R_2$ can be varied in several useful ways. For example, $R_2$ can be modified to include additional charged groups in order to further retard leakage from the cell, an additional fluorine in order to serve as a chemical shift reference, or $R_2$ can represent a polymer such as a peptide.

Another embodiment of the invention includes compounds which are represented by the Formula II:

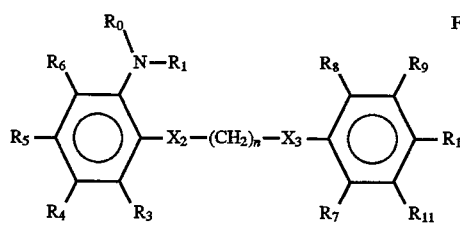

Formula II $R_0$ and $R_1$ are selected independently from the group consisting of hydrogen, alkyl, aryl, substituted alkyl, substituted aryl, carboxyl, carboxyalkyl, substituted carboxyalkyl, heteroaryl, and substituted heteroaryl. $R_3$–$R_{11}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $X_2$ and $X_3$ are selected independently from the group consisting of oxygen, nitrogen, sulfur, and —$CH_2$—, and n is 0, 1, 2, or 3. At least one of $R_3$–$R_6$ and one of $R_7$–$R_{11}$ is fluorine, and at least one of $X_2$ and $X_3$ is —$CH_2$— when n is zero.

A preferred example of a compound of Formula II is where $R_0$ is ethyl, $R_1$ is carboxymethyl, $R_4$ and $R_7$ are fluorine, $R_{10}$ is $N(CH_2CO_2H)_2$, $X_2$ and $X_3$ are oxygen, n is 2, and $R_3$, $R_5$, $R_6$, $R_8$, $R_9$, and $R_{11}$ are hydrogen. Another preferred example of a compound of Formula II is where $R_0$ is ethyl, $R_1$ is carboxymethyl, $R_4$ and $R_7$ are fluorine, $R_{10}$ is carboxyl, $X_2$ is oxygen, $X_3$ is methyl, n is zero, and $R_3$, $R_5$, $R_6$, $R_8$, $R_9$, and $R_{11}$ are hydrogen.

In another embodiment, the invention includes compounds as represented in Formula III:

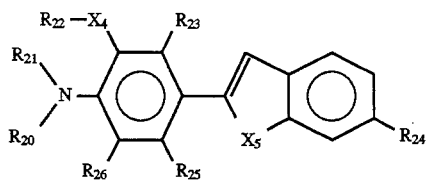

Formula III $R_{20}$–$R_{22}$ are selected independently from the group consisting of hydrogen, alkyl, aryl, substituted alkyl, substituted aryl, carboxyl, carboxyalkyl, substituted carboxyalkyl, heteroaryl and substituted heteroaryl. $R_{23}$–$R_{26}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $X_4$ and $X_5$ are selected independently from the group consisting of oxygen, nitrogen, and sulfur.

A preferred example of a compound of Formula III is:

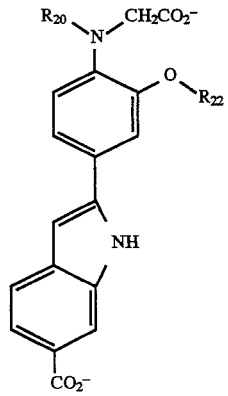

Another example of a preferred compound of Formula III is where $R_{20}$ is ethyl, $R_{21}$ and $R_{22}$ are carboxymethyl, $R_{24}$ is carboxyl, $X_4$ and $X_5$ are oxygen, and $R_{23}$, $R_{25}$, and $R_{26}$ are hydrogen.

In yet another embodiment, the invention includes compounds represented by Formula IV:

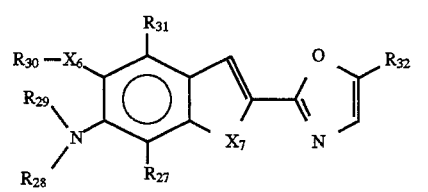

Formula IV $R_{27}$, $R_{31}$ and $R_{32}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $R_{28}$–$R_{30}$ are selected independently from the group consisting of hydrogen, alkyl, aryl, substituted alkyl, substituted aryl, carboxyl, carboxyalkyl, substituted carboxyalkyl, heteroaryl, and substituted heteroaryl. $X_6$ and $X_7$ are selected independently from the group consisting of oxygen, nitrogen, and sulfur.

However, $R_{28}$–$R_{30}$ are not all $CH_2CO_2CH_2OCOCH_3$ when $R_{32}$ is $CO_2CH_2OCOCH_3$, $X_6$ and $X_7$ are oxygen, and $R_{27}$ and $R_{31}$ are hydrogen; $R_{28}$–$R_{30}$ are not all $CH_2CO_2H$ when $R_{32}$ is $CO_2H$, $X_6$ and $X_7$ are oxygen, and $R_{27}$ and $R_{31}$ are hydrogen; and $R_{28}$ and $R_{29}$ are not both $CH_2CO_2H$ when $R_{30}$ is $(CH_2)_2O(C_6H_3CH_3N(CH_2CO_2H)_2)$, $R_{32}$ is $CO_2H$, $X_6$ and $X_7$ are oxygen, and $R_{27}$ and $R_{31}$ are hydrogen.

An example of a preferred compound of Formula IV is where $R_{27}$ and $R_{31}$ are hydrogen, $R_{28}$ and $R_{30}$ are carboxymethyl, $R_{29}$ is ethyl, $R_{32}$ is carboxyl, and $X_6$ and $X_7$ are oxygen.

In another embodiment, the invention includes compounds comprising Formula V:

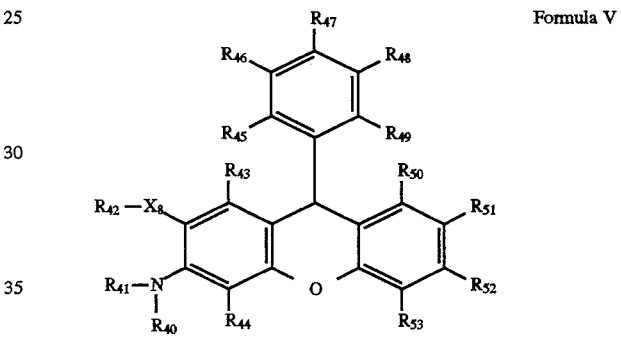

Formula V $R_{40}$–$R_{42}$ are selected independently from the group consisting of hydrogen, alkyl, aryl, substituted alkyl, substituted aryl, carboxyl, carboxyalkyl, substituted carboxyalkyl, heteroaryl and substituted heteroaryl. $R_{43}$–$R_{53}$ are selected independently from the group consisting of hydrogen, alkyl, aryl, substituted alkyl, substituted aryl, hydroxyl, ether, thioether, substituted amino, halogen, heteroaryl, substituted heteroaryl, carboxyl, carboxyalkyl, substituted carboxyalkyl, and amido. $X_8$ is selected from the group consisting of oxygen, nitrogen, and sulfur, and at least one of $R_{45}$–$R_{49}$ is —$CO_2H$.

A preferred example of a compound of this Formula V comprises the formula:

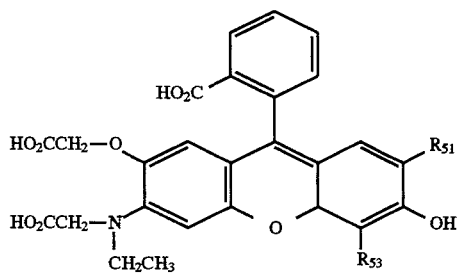

Another example of a preferred compound comprises the formula:

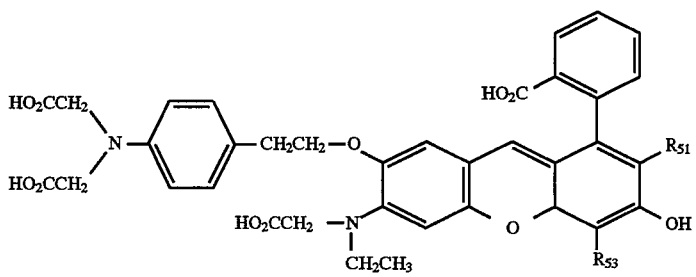

In still another embodiment, the present invention includes a compound as shown in Formula VI:

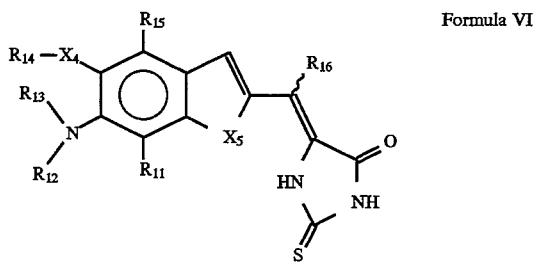

Formula VI $R_{11}$, $R_{15}$ and $R_{16}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $R_{12}$–$R_{14}$ are selected independently from the group consisting of hydrogen, alkyl, aryl, substituted alkyl, substituted aryl, heteroaryl, substituted heteroaryl, carboxyl, carboxyalkyl and substituted carboxyalkyl. $X_4$ and $X_5$ are selected independently from the group consisting of oxygen, nitrogen, and sulfur.

A preferred embodiment of this compound comprises the formula:

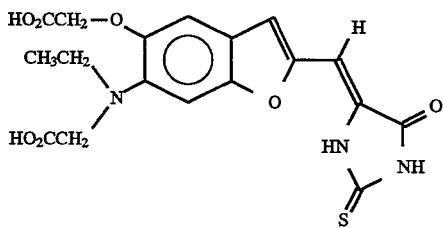

In other embodiments, the present invention includes methods of measuring the pH of a sample which comprise introducing a standard and an indicator of the present invention into the sample, recording the $^{19}$F NMR or the fluorescence-excitation spectra of the sample, comparing the chemical shift of the $^{19}$F nuclei or fluorescence-excitation spectra of the indicator relative to that of the standard and comparing this relative chemical shift or fluorescence-excitation spectra with the relative chemical shift or fluorescence-excitation spectra at known pH values, to thereby determine the pH of the sample.

In a preferred embodiment, the present invention includes methods for measuring intracellular pH. These methods comprise introducing a standard and an indicator of the present invention into a sample containing cells, measuring the relative chemical shift or the fluorescence-excitation spectra of the sample by comparing the chemical shift or fluorescence-excitation spectra of the indicator relative to that of the standard and comparing the relative chemical shift or fluorescence-excitation spectra with the relative chemical shift or fluorescence-excitation spectra at known pH values, to thereby determine the intracellular pH of the sample. As has been noted, some of the indicators of the present invention include internal references and as such are herein included in discussions of 'a standard and an indicator'.

An additional embodiment of the invention includes a method to diagnose a patient suspected of having a mammalian disease which disease is characterized by a change in the intracellular pH, which method comprises collecting a sample of cells from a patient; introducing to the sample, a compound of the invention; measuring the spectrum of the sample, and comparing the spectrum to spectra at known pH; and comparing the pH of the sample to the pH of a disease-free sample to detect the presence of such a disease. Preferred embodiments of this method include recording the $^{19}$F or the fluorescence-excitation spectra of the sample as described herein, and using the compounds described elsewhere in the invention.

BRIEF DESCRIPTION OF THE DRAWINGS

FIG. 3A shows the $^{19}$F chemical shift of the intracellular indicator NEAP. FIG. 3B shows the change in the 19F NMR spectrum resulting from the addition of extracellular 5F NEAP-1, demonstrating that this compound does not cross the cellular membrane in appreciable amounts. The resonance associated with intracellular NEAP is denoted as "INTRA"; the resonance associated with extracellular NEAP is denoted as "EXTRA".

DESCRIPTION OF THE PREFERRED EMBODIMENT

I. Definitions and General Parameters

Figure 1:
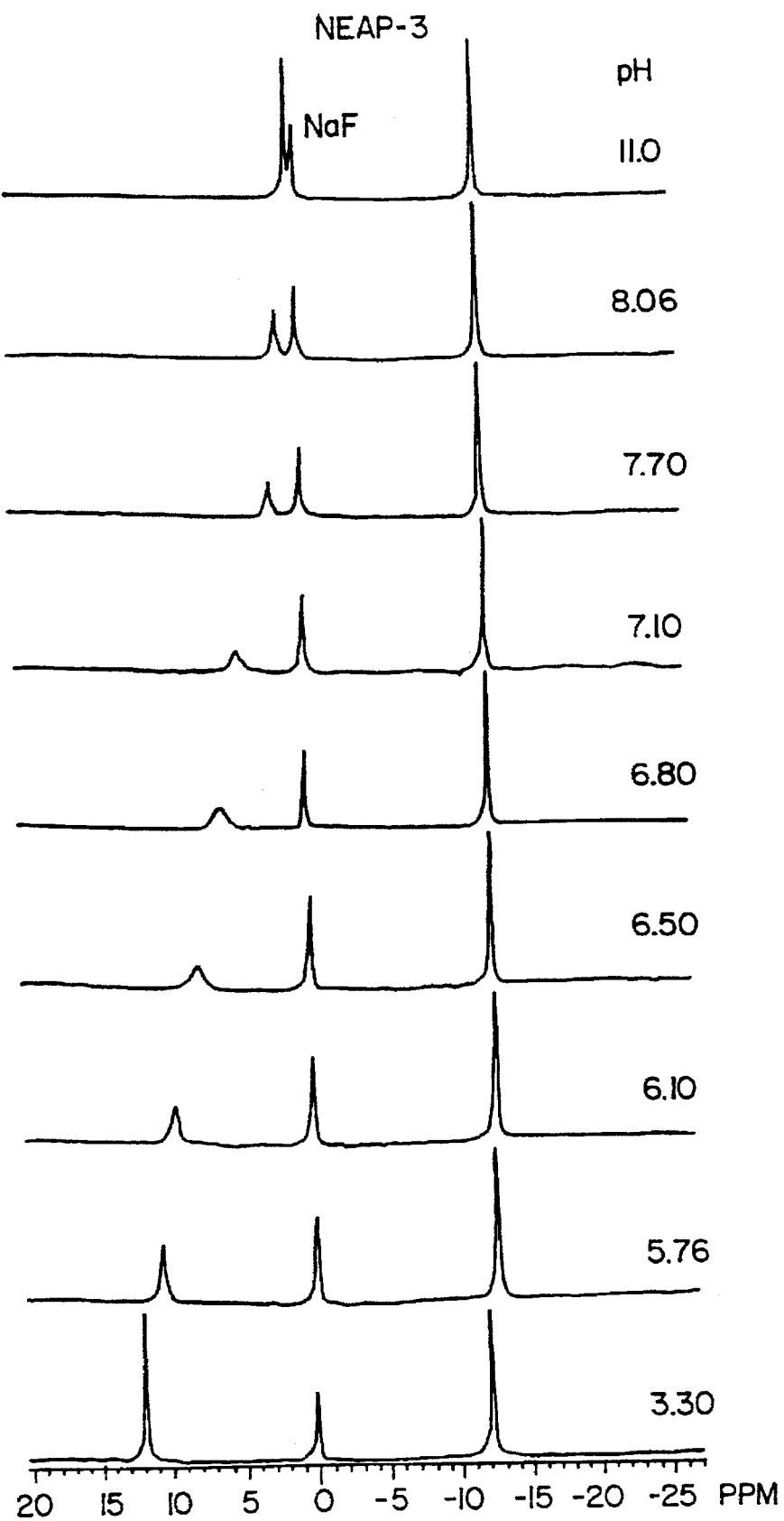
FIG. 1 shows fluorine-19 NMR spectra as a function of pH for 5F NEAP-3. The sample also contained Sodium Flouride as an internal chemical shift standard.

The following definitions are set forth to illustrate and define the meaning and scope of the various terms used to describe the invention herein.

"Alkyl" refers to a cyclic, branched or straight chain alkyl group of one to six carbon atoms, which can optionally be unsubstituted or substituted with, e.g., amino, aryl, heteroaryl, aryloxy, nitro, cyano, sulfonic acid, carbonyl, halogen, lower alkyl, lower alkoxy, lower alkylthio, trifluoromethyl, lower acyloxy, and hydroxyl. This term is further exemplified by such groups as methyl, ethyl, n-propyl, i-propyl, n-butyl, t-butyl, i-butyl (or 2-methylpropyl), cyclopropylmethyl, i-amyl, n-amyl, and hexyl.

"Alkoxy" refers to the group —$OR_1$ wherein $R_1$ is a lower alkyl group.

"Amino" and "Substituted Amino" refer to the group —$NR_1R_2$, where $R_1$ and $R_2$ are independently hydrogen, lower alkyl or aryl.

"Amido" refers to the group —$ONH_2$.

"Aryl" or "Ar" refers to an aromatic carbocyclic group having a single ring (e.g., phenyl) or multiple condensed rings in which at least one ring is aromatic, (e.g., 1,2,3,4-tetrahydronaphthyl, naphthyl, or anthryl), which can optionally be unsubstituted, or substituted with, e.g., amino, nitro, cyano, sulfonic acid, carbonyl, halogen, lower alkyl, lower alkoxy, lower alkylthio, trifluoromethyl, lower acyloxy, and hydroxyl.

"Carboxyl" or "carboxylic acid" refers to the group —COOH.

"Carboxyalkyl" refers to the group —RCOOH, where R is an alkyl or substituted alkyl group.

"Cyano" refers to the group —CN.

"Ether" refers to the group —O—.

"Halogen" refers to fluorine, bromine, chlorine, and iodine atoms.

"Heteroaryl" or "HetAr" refers to a saturated, unsaturated, or aromatic carbocyclic group having a single ring (e.g., morpholino, pyridyl or furyl) or multiple condensed rings (e.g., quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, lower alkylthio, trifluoromethyl, lower acyloxy, and hydroxyl.

"Hydroxy" or "hydroxyl" refers to the group —OH.

"Nitro" refers to the group —$NO_2$.

"Thioether" refers to the group —S—.

II. Intracellular pH Indicators

The present invention includes compounds and methods for determining intracellular pH using $^{19}F$ NMR spectroscopy and fluorescence methods. These compounds exhibit sufficient sensitivity to the concentration of protons to function as effective intracellular pH indicators, and chemical characteristics that minimize leakage from the cells or undesired interactions with cellular constituents on the time scale of the measurements. Such measurements are useful in monitoring cell functions and in diagnosing human diseases.

A. Fluorinated NMR Indicators

One embodiment of the instant invention includes fluorine containing compounds, the $^{19}F$ chemical shift of which exhibit a high sensitivity to the local pH. As a result of this sensitivity, these compounds can serve as indicators to monitor the pH of intracellular organelles if they are loaded into these organelles in sufficient concentration to permit observation of the corresponding NMR resonances, and if the pH of the organelle differs sufficiently (generally more than about >0.1 pH unit) from that of the cytosol.

One embodiment of the invention includes compounds which are represented by Formula I:

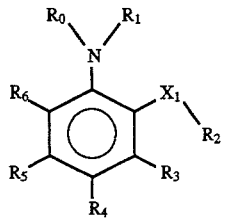

Formula I $R_0$–$R_2$ are selected independently from the group consisting of hydrogen, alkyl, aryl, substituted alkyl, substituted aryl, carboxyl, carboxyalkyl, substituted carboxyalkyl, heteroaryl and substituted heteroaryl. $R_3$–$R_6$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $X_1$ is selected from the group consisting of oxygen, nitrogen, and sulfur.

However, (a) $R_0$, $R_1$ and $R_2$ are not all —$CH_2CO_2H$ or —$CH_2CO_2CH_3$ when $X_1$ is oxygen, $R_4$ is fluorine or hydrogen, $R_5$ is hydrogen, fluorine or methyl, and $R_3$ and $R_6$ are hydrogen; (b) $R_0$ and $R_1$ are not both —$CH_2CO_2H$ when $X_1$ is oxygen, $R_4$ is fluorine and $R_3$, $R_5$ and $R_6$ are hydrogen, and $R_2$ is —$(CH_2)_2O(CH_2)_2N(CH_2CO_2H)_2$; (c) $R_0$ and $R_1$ are not both —$CH_2CO_2H$ when $X_1$ is oxygen, $R_3$, $R_4$, $R_5$ and $R_6$ are fluorine or hydrogen, and $R_2$ is —$(CH_2)_2O(C_6H_3N(CH_2CO_2H)_2F)$; (d) $R_0$ and $R_1$ are not both —$CH_2CO_2H$ or —$CH_2CO_2CH_3$ when $X_1$ is oxygen, $R_4$ is fluorine, $R_5$ is methyl, —$C(CH_3)_2CH_2CO_2H$ or —$C(CH_3)_2CH_2CO_2CH_3$, and $R_3$ and $R_6$ are hydrogen; (e) $R_0$ and $R_1$ are not both —$CH_2CO_2H$ or —$CH_2CO_2CH_3$ when $X_1$ is oxygen, $R_4$ is fluorine, $R_5$–$R_6$ are hydrogen, and $R_2$ is an (8-amino-2-quinoline)methyl; (f) $R_0$ and $R_1$ are not both —$CH_2CO_2CH_2C_6H_5$ when $X_1$ is oxygen, $R_4$ is fluorine, $R_3$, $R_5$ and $R_6$ are hydrogen, and $R_2$ is —$(CH_2)_2O(CH_2)_2N(CH_2CO_2CH_2C_6H_5)_2$; and (g) $R_0$ is not —$C(CH_3)_2CO_2CH_3$ or —$C(CH_3)_2CO_2H$ when $R_1$ is hydrogen or methyl, $X_1$ is oxygen, $R_4$ is fluorine, and $R_3$, $R_5$ and $R_6$ are hydrogen; and (h) at least one of $R_3$–$R_6$ is fluorine.

A preferred example of a compound of Formula I is where $R_0$ is selected from the group consisting of alkyl and substituted alkyl; another preferred example is where $R_0$ is selected from the group consisting of alkyl and substituted alkyl and $R_1$ is selected from the group consisting of carboxyl, carboxyalkyl, or substituted carboxyalkyl.

An additional preferred embodiment is where $R_0$ is ethyl, and $R_1$ and $R_2$ are carboxymethyl. Still another preferred embodiment is one wherein $R_0$ is ethyl, $R_1$ and $R_2$ are carboxymethyl, and $R_3$–$R_6$ are selected independently from the group consisting of hydrogen and fluorine.

A particularly preferred example of a compound of Formula I is where $R_0$ is ethyl; $R_1$ and $R_2$ are carboxymethyl; $R_3$, $R_5$ and $R_6$ are hydrogen; $R_4$ is fluorine; and $X_1$ is oxygen. Another particularly preferred embodiment of a compound of Formula I is where $R_0$ is ethyl; $R_1$ and $R_2$ are carboxymethyl; $R_3$, $R_4$ and $R_5$ are hydrogen; $R_6$ is fluorine; and $X_1$ is oxygen.

Another embodiment of the invention includes compounds which are represented by Formula II:

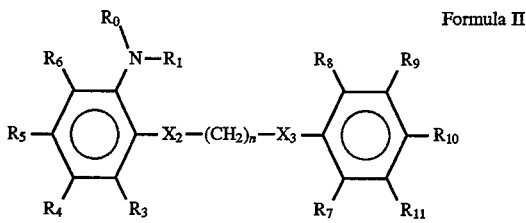

Formula II

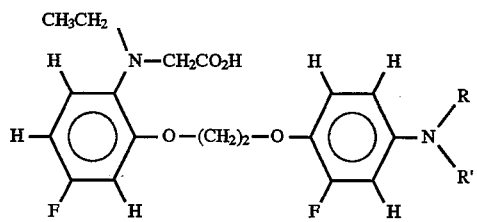

$R_0$ and $R_1$ are selected independently from the group consisting of hydrogen, alkyl, aryl, substituted alkyl, substituted aryl, carboxyl, carboxyalkyl, substituted carboxyalkyl, heteroaryl and substituted heteroaryl. $R_3$–$R_{11}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl, and amido. $X_2$ and $X_3$ are selected independently from the group consisting of oxygen, nitrogen, sulfur, and —$CH_2$—, and n is 0, 1, 2, or 3. At least one of $R_3$–$R_6$ and one of $R_7$–$R_{11}$ is fluorine, and at least one of $X_2$ and $X_3$ is —$CH_2$— when n is zero.

A preferred example of a compound of Formula II is where $R_1$ is a carboxyalkyl ester. Another preferred embodiment is one wherein $R_1$ is a substituted carboxyalkyl and $R_3$–$R_{11}$ are selected independently from the group consisting of hydrogen and fluorine. Yet another preferred embodiment is where $R_1$ is a substituted carboxyalkyl, $R_3$–$R_{11}$ are selected independently from the group consisting of hydrogen and fluorine, and $X_2$ and $X_3$ are oxygen.

An additional preferred embodiment of the invention is a compound which comprises the formula:

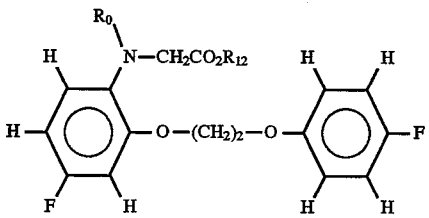

wherein $R_{12}$ is selected from the group consisting of hydrogen, alkyl, aryl, substituted alkyl, substituted aryl, carboxyl, carboxyalkyl, substituted carboxyalkyl, heteroaryl and substituted heteroaryl.

Yet another preferred example is a compound which comprises the formula:

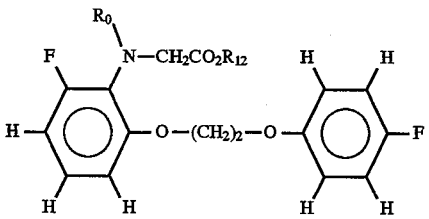

Another preferred embodiment of this Formula includes compounds which comprise the formula:

wherein R and R' are selected independently from the group consisting of hydrogen, alkyl, aryl, substituted alkyl, substituted aryl, carboxyl, carboxyalkyl, substituted carboxyalkyl, heteroaryl, and substituted heteroaryl.

A particularly preferred example of a compound of Formula II is where $R_0$ is ethyl, $R_1$ is carboxymethyl, $R_4$ and $R_7$ are fluorine, $R_{10}$ is $N(CH_2CO_2H)_2$, $X_2$ and $X_3$ are oxygen, n is 2, and $R_3$, $R_5$, $R_6$, $R_8$, $R_9$, and $R_{11}$ are hydrogen. Another preferred example of a compound of Formula II is where $R_0$ is ethyl, $R_1$ is carboxymethyl, $R_4$ and $R_7$ are fluorine, $R_{10}$ is carboxyl, $X_2$ is oxygen, $X_3$ is methyl, n is zero, and $R_3$, $R_5$, $R_6$, $R_8$, $R_9$, and $R_{11}$ are hydrogen.

B. Fluorescent Analogs

In another embodiment, the invention includes compounds as represented in Formula III:

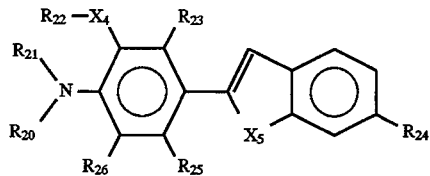

$R_{20}$–$R_{22}$ are selected independently from the group consisting of hydrogen, alkyl, aryl, substituted alkyl, substituted aryl, carboxyl, carboxyalkyl, substituted carboxyalkyl, heteroaryl and substituted heteroaryl. $R_{23}$–$R_{26}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $X_4$ and $X_5$ are selected independently from the group consisting of oxygen, nitrogen, and sulfur.

In a preferred example of a compound of Formula III, $R_{20}$ is an alkyl or substituted alkyl. In another preferred example, $R_{20}$ is an alkyl or substituted alkyl, and $R_{21}$ is selected from the group consisting of carboxyl, carboxyalkyl, or substituted carboxyalkyl. Yet another preferred example is where $R_{20}$ is an alkyl or substituted alkyl, and $R_{21}$ and $R_{22}$ are independently selected from group consisting of carboxyl, carboxyalkyl, or substituted carboxyalkyl. In additional preferred embodiments, $R_{20}$ is an alkyl or substituted alkyl, and $R_{21}$ and $R_{22}$ are independently selected from group consisting of carboxyl, carboxyalkyl, or substituted carboxyalkyl, and $X_4$ is oxygen.

An example of a particularly preferred compound of Formula III is where $R_{20}$ is ethyl, $R_{21}$ and $R_{22}$ are carboxymethyl, $R_{24}$ is carboxyl, $X_4$ and $X_5$ are oxygen, and $R_{23}$, $R_{25}$, and $R_{26}$ are hydrogen. Another example of a preferred embodiment of a compound of Formula III is where $R_{20}$ is ethyl, $R_{21}$ and $R_{22}$ are carboxymethyl, $R_{24}$ is carboxyl, $X_4$ is oxygen, $X_5$ is —NH—, and $R_{23}$, $R_{25}$, and $R_{26}$ are hydrogen.

In yet another embodiment, the invention includes compounds represented by Formula IV:

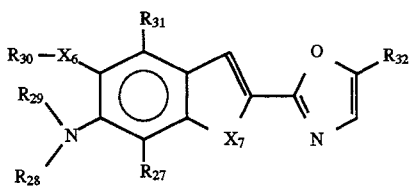

$R_{27}$, $R_{31}$ and $R_{32}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $R_{28}$–$R_{30}$ are selected independently from the group consisting of hydrogen, alkyl, aryl, substituted alkyl, substituted aryl, carboxyl, carboxyalkyl, substituted carboxyalkyl, heteroaryl and substituted heteroaryl. $X_6$ and $X_7$ are selected independently from the group consisting of oxygen, nitrogen, and sulfur.

However, $R_{28}$–$R_{30}$ are not all —$CH_2CO_2CH_2OCOCH_3$ when $R_{32}$ is —$CO_2CH_2OCOCH_3$, $X_6$ and $X_7$ are oxygen, and $R_{27}$ and $R_{31}$ are hydrogen; $R_{28}$–$R_{30}$ are not all —$CH_2CO_2H$ when $R_{32}$ is $CO_2H$, $X_6$ and $X_7$ are oxygen, and $R_{27}$ and $R_{31}$ are hydrogen; and $R_{28}$ and $R_{29}$ are not both —$CH_2CO_2H$ when $R_{30}$ is —$(CH_2)_2O(C_6H_3CH_3N(CH_2CO_2H)_2)$, $R_{32}$ is —$CO_2H$, $X_6$ and $X_7$ are oxygen, and $R_{27}$ and $R_{31}$ are hydrogen.

A preferred example of a compound of Formula IV is where $R_{28}$ is selected from the group consisting of alkyl and substituted alkyl. Another preferred example is where $R_{28}$ is selected from the group consisting of alkyl and substituted alkyl, and $R_{29}$ is selected from the group consisting of carboxyl, carboxyalkyl, and substituted carboxyalkyl.

Another example of a preferred compound of Formula IV is where $R_{27}$ and $R_{31}$ are hydrogen, $R_{29}$ and $R_{30}$ are carboxymethyl, $R_{32}$ is carboxyl, and $X_6$ and $X_7$ are oxygen. Yet another example of a preferred compound of Formula IV is where $R_{27}$ and $R_{31}$ are hydrogen, $R_{29}$ and $R_{30}$ are carboxymethyl, $R_{28}$ is ethyl, $R_{32}$ is carboxyl, and $X_6$ and $X_7$ are oxygen.

In another embodiment, the invention includes compounds comprising Formula V:

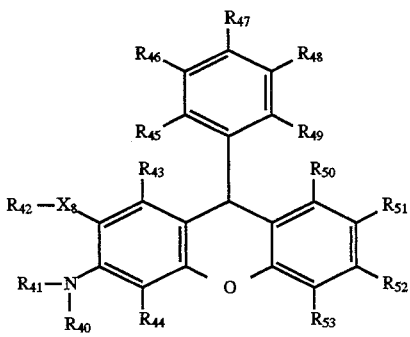

$R_{40}$–$R_{42}$ are selected independently from the group consisting of hydrogen, alkyl, aryl, substituted alkyl, substituted aryl, carboxyl, carboxyalkyl, substituted carboxyalkyl, heteroaryl and substituted heteroaryl. $R_{43}$–$R_{53}$ are selected independently from the group consisting of hydrogen, alkyl, aryl, substituted alkyl, substituted aryl, hydroxyl, ether, thioether, substituted amino, halogen, heteroaryl, substituted heteroaryl, carboxyl, carboxyalkyl, substituted carboxyalkyl and amido. $X_8$ is selected from the group consisting of oxygen, nitrogen, and sulfur, and at least one of $R_{45}$–$R_{49}$ is —$CO_2H$.

A preferred example of a compound of Formula V is where $R_{52}$ is hydroxyl. Another preferred example is where $R_{52}$ is hydroxyl, and $X_8$ is oxygen. In yet another preferred example of a compound of Formula V, $R_{52}$ is hydroxyl, $X_8$ is oxygen, and $R_{40}$ is selected from the group consisting of alkyl and substituted alkyl.

An additional preferred embodiment of this Formula is where $R_{52}$ is hydroxyl, $X_8$ is oxygen, $R_{40}$ is selected from the group consisting of alkyl and substituted alkyl, and $R_{41}$ is selected from the group consisting of carboxyl, carboxyalkyl, or substituted carboxyalkyl.

A particularly preferred example of a compound of this Formula V comprises the formula:

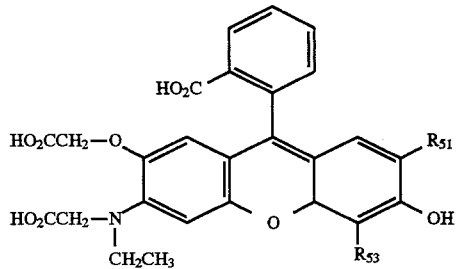

Another example of a particularly preferred compound of Formula V comprises the formula:

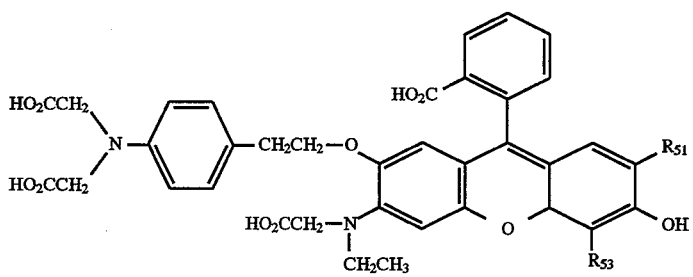

In still another embodiment, the present invention includes a compound as shown in Formula VI:

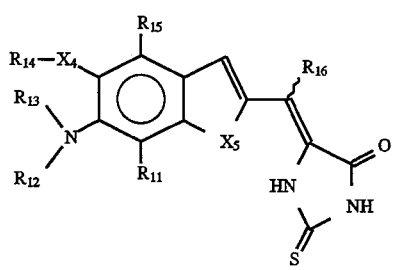

$R_{11}$, $R_{15}$ and $R_{16}$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido. $R_{12}$–$R_{14}$ are selected independently from the group consisting of hydrogen, alkyl, aryl, substituted alkyl, substituted aryl, heteroaryl, substituted heteroaryl, carboxyl, carboxyalkyl and substituted carboxyalkyl. $X_4$ and $X_5$ are selected independently from the group consisting of oxygen, nitrogen, and sulfur.

A preferred embodiment of this compound comprises the formula:

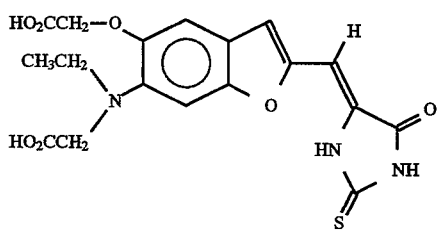

III. Synthesis

The synthesis of the compounds of the invention is achieved readily using materials and techniques which are well-known in the chemical arts (see, e.g., March, Advanced Organic Chemistry (Wiley 1992); Larock, Comprehensive Organic Transformations, (VCH 1989); Furhiss, et al., Vogel's Textbook of Practical Organic Chemistry 5th ed. (Longman 1989); and Green and Wuts, Protective Groups In Organic Synthesis (Wiley 1991)). All of the compounds of the invention may be synthesized by analogy to the examples below. A. NMR Indicators N-ethyl-2-amino-5-fluorophenol-N,O-diacetic acid, "5F NEAP-1", was prepared as shown in Scheme 1:

Scheme 1

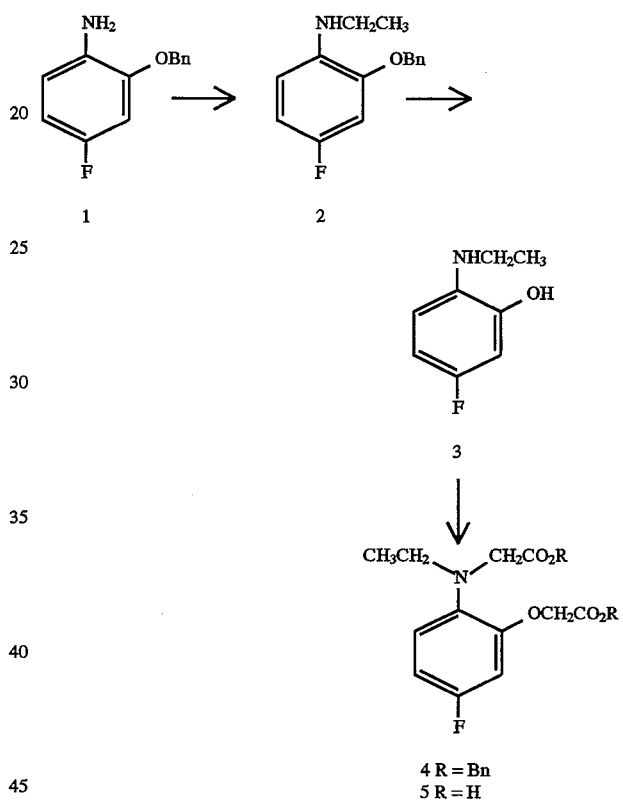

4 R = Bn
5 R = H

Starting with commercially available 2-benzyloxy-4-fluoroaniline (1), monoethylation to form the N-ethyl derivative (2) was effected by reductive alkylation using sodium borohydride/acetic acid ($NaBH_4/CH_3CO_2H$). Removal of the benzyl protecting group by catalytic hydrogenation with palladium/carbon (Pd/C) in ethyl acetate (EtOAc) to form (3), and subsequent dialkylation of the amino and phenolic hydroxyl moieties with benzyl bromoacetate, resulted in the dibenzyl ester (4), which is converted by standard methods, e.g., hydrogenolysis, to N-ethyl-2-amino-5-fluorophenol-N,O-diacetic acid (5), "5F NEAP-1".

A second compound was prepared which contained an additional fluorine to serve as an internal reference. This indicator, referred to as "5F NEAP-2", was prepared as shown in Scheme 2:

Scheme 2

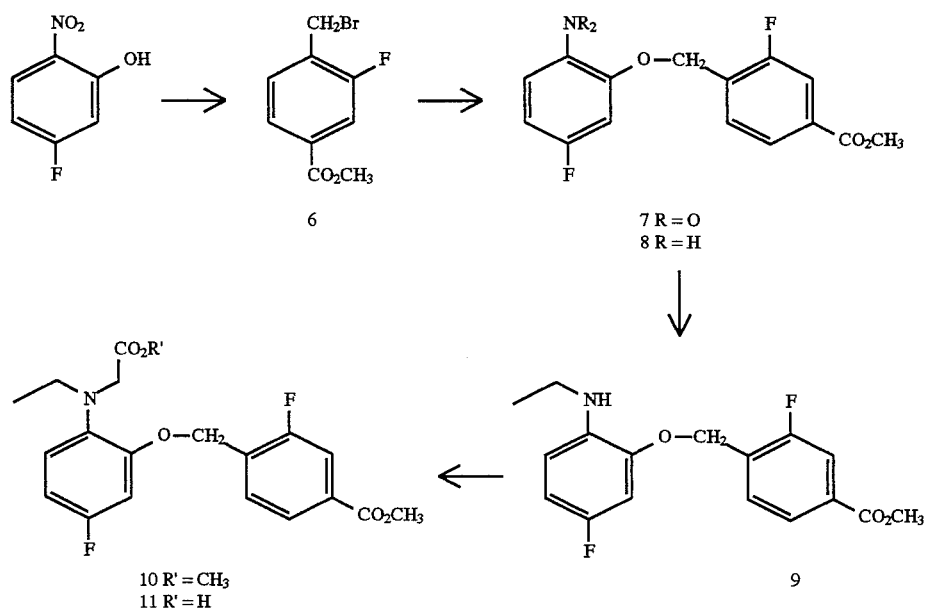

Commercially available 5-fluoro-2-nitrophenol was coupled with 2-fluoro-3-bromomethylbenzoic acid methyl ester (6) using potassium carbonate in dimethylformamide (DMF) to yield the coupled nitro phenolic ether (7). The nitro group was reduced to the corresponding amine (8) by hydrogenation over Pd/C. Compound 8 was alkylated by reaction with sodium borohydride and acetic acid to give the N-ethyl amine (9), which was subsequently alkylated with methylbromoacetate using Proton Sponge® to yield the methyl ester of 5F NEAP-2 (10). Saponification with sodium hydroxide and ethanol in water gave the free acid form of the indicator (11).

A more highly charged analog, "5F NEAP-3", was prepared as follows (Scheme 3):

Scheme 3

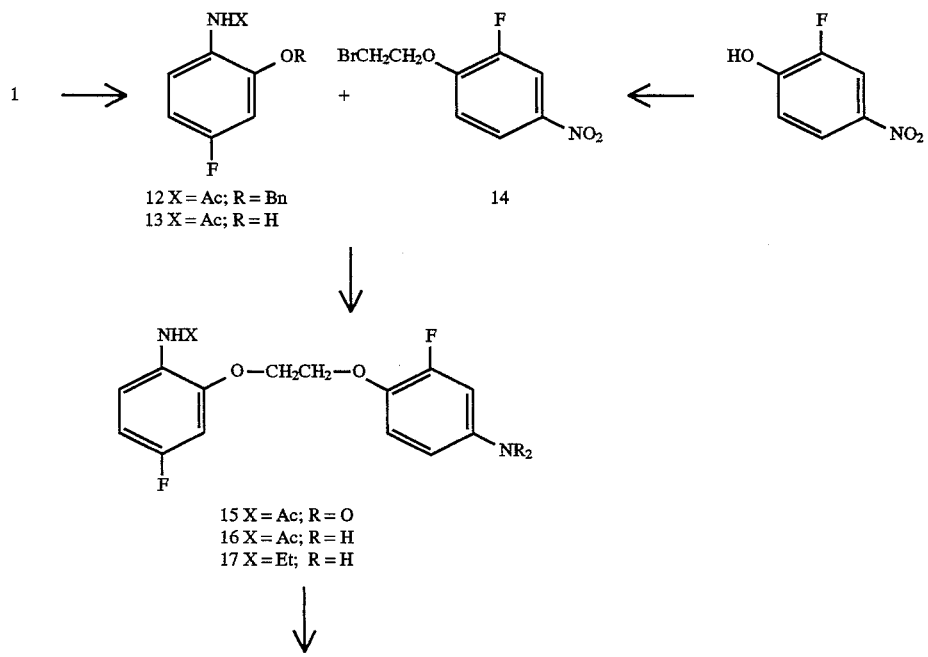

-continued
Scheme 3

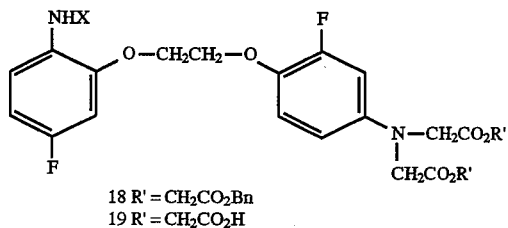

18 R' = CH₂CO₂Bn
19 R' = CH₂CO₂H

The N-acetylated benzyl ester (12) of 2-amino-5-fluorophenol (1) was prepared by reaction of (1) with acetic anhydride/triethylamine ($Ac_2O/Et_3N$). The benzyl group was removed by hydrogenolysis to form the product (13) which was was reacted with 2-fluoro-4-nitrophenol bromoethyl ester (14) to yield diether (15). Bromoethylester (14) was formed by the reaction of 4-nitro-2-fluorophenol with 1,2-dibromoethane. Reduction of the nitro and acetyl groups to form first acetamide (16) and then ethylamine (17), followed by alkylation with benzyl bromoacetate, yielded the benzyl ester form of the indicator (18). The free acid (19) was prepared by hydrogenolysis of the benzyl esters.

B. Fluorescent Indicators

The synthesis of fluorescent indicators derived from 2-aminophenol can be effected by analogy with published procedures for the synthesis of the corresponding calcium ion chelators (Grynkiewicz et al., *J. Biol. Chem.* 260, 3440–3450; 1985; Smith et al. *J. Chem. Soc. Perkin Trans.* 2, 1195–1204; 1993) and magnesium ion chelators (Levy, et al., *Biochemistry* 27, 4041–4048; 1988; Raju et al., *Am. J. Physiol.* 256, *Cell Physiol.* 25; C540–C548; 1989). One pH sensitive analog of the type of chelator described in the above references can be prepared as shown in the following scheme, and as outlined below. This indicator, "NEAP-FURA1", is sensitive to changes in local pH, rather than to changes in physiological $Mg^{2+}$ concentrations as for the compounds previously described.

As shown in Scheme 4 below, aniline derivatives (25)–(29) can be prepared by reduction of the protected nitrohydroquinones (20)–(24) using standard methods such as hydrogenation over Pd/C. The N-ethyl derivatives (35)–(39) can be formed either in one step from (25)–(29) using $NaBH_4$/acetic acid, or utilizing a two step procedure by first treating (25)–(29) with acetic anhydride/pyridine to form (30)–(34), followed by reduction with lithium aluminum hydride to yield (35)–(39). Selective removal of the various protecting group ortho to the amino function in (35)–(39) to yield (40) can be acheived using standard methods appropriate for each group (see, e.g., Green and Wuts, supra). Alkylation with methyl bromoacetate will give (41). Removal of the benzyl group by treating with Pd/C and $H_2$ will result in (42), which is cyclized to (43) and (44) (NEAP-FURA1) using published procedures (see, Raju et al., *Am. J. Physiol.* 256 (Cell Physiol. 25; C540–C548; 1989).

Scheme 4

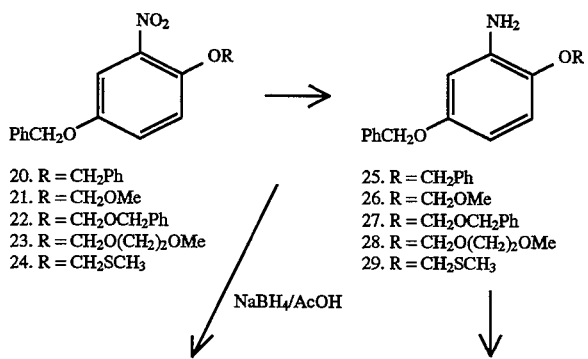

20. R = CH₂Ph
21. R = CH₂OMe
22. R = CH₂OCH₂Ph
23. R = CH₂O(CH₂)₂OMe
24. R = CH₂SCH₃

25. R = CH₂Ph
26. R = CH₂OMe
27. R = CH₂OCH₂Ph
28. R = CH₂O(CH₂)₂OMe
29. R = CH₂SCH₃

NaBH₄/AcOH

-continued
Scheme 4

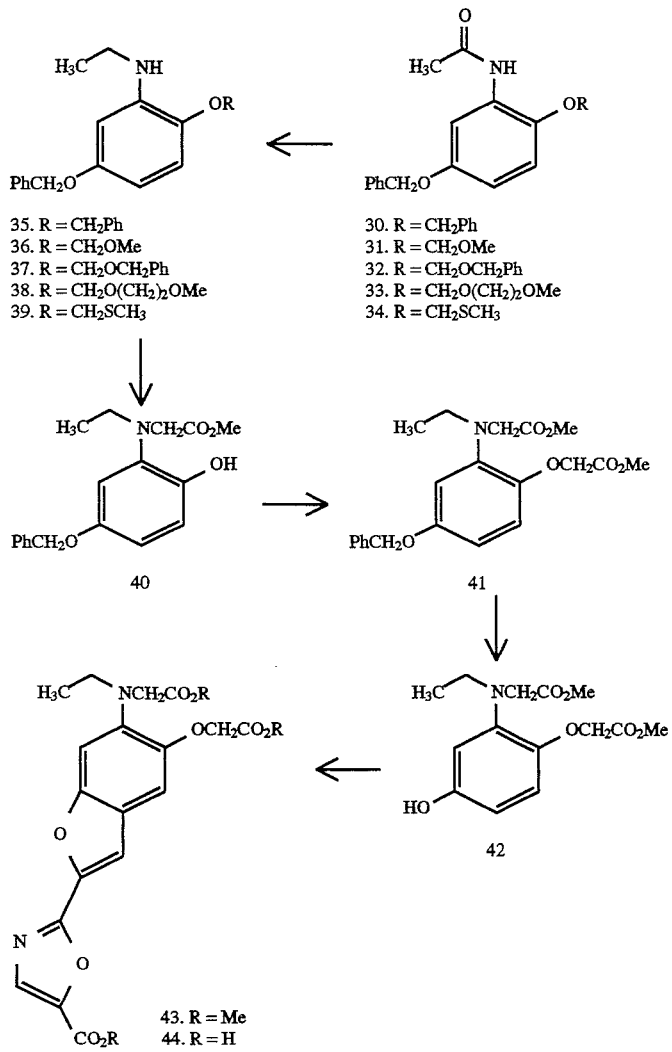

35. R = CH₂Ph
36. R = CH₂OMe
37. R = CH₂OCH₂Ph
38. R = CH₂O(CH₂)₂OMe
39. R = CH₂SCH₃

30. R = CH₂Ph
31. R = CH₂OMe
32. R = CH₂OCH₂Ph
33. R = CH₂O(CH₂)₂OMe
34. R = CH₂SCH₃

40

41

42

43. R = Me
44. R = H

Another indicator, "NEAP-FURA2", which is a pH sensitive analog of the calcium ion indicator described by Grynkiewicz et al. (*J. Biol. Chem.* 260, 3440–3450; 1985), can be prepared as shown and described below with reference to Scheme 5.

Phenol intermediate (45) can be prepared from (30)–(34) as previously described with respect to (40). Reaction of (45) with 2-(4-nitrobenzyloxy)-1-bromoethane (46) will yield diether (47). The requisite N-ethyl group of (48) can be added by lithium aluminum hydride reduction of the N-acetyl derivative (47). Alkylation (methyl bromoacetate) lead to (49). Removal of the protecting benzyl group of (49) by Pd/C,H₂ yields free phenol (50). Conversion to (51) and elaboration to (52) can be done using published procedures (Grynkiewicz et al., supra). Reduction of the nitro group (Pt/C or Pd/C, H₂) will yield (53). Alkylation (methyl bromoacetate) to (54) and saponification (1. NaOH/aqueous methanol; 2. H+) will produce the indicator NEAP-FURA2 (55).

Scheme 5
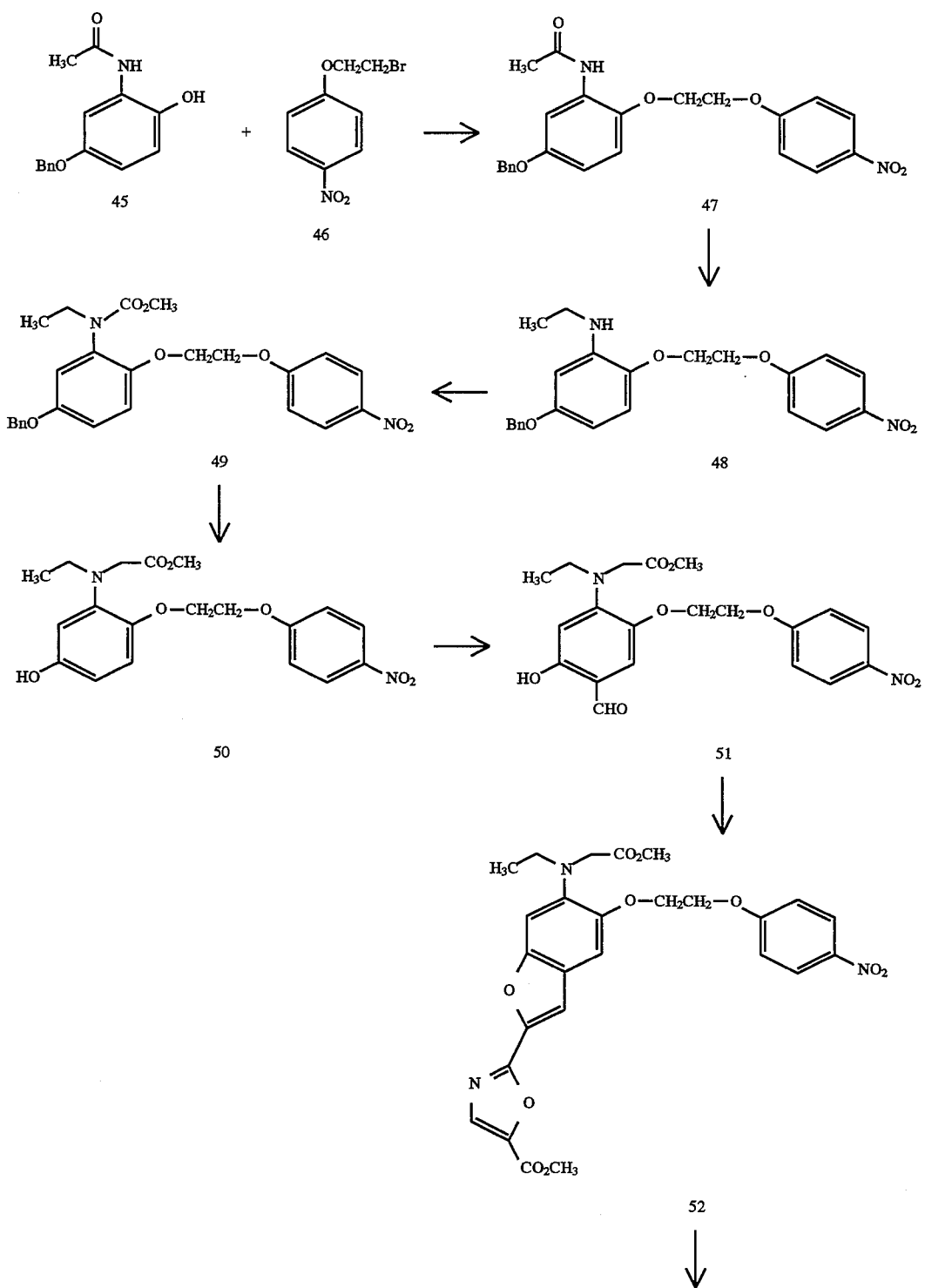

-continued
Scheme 5

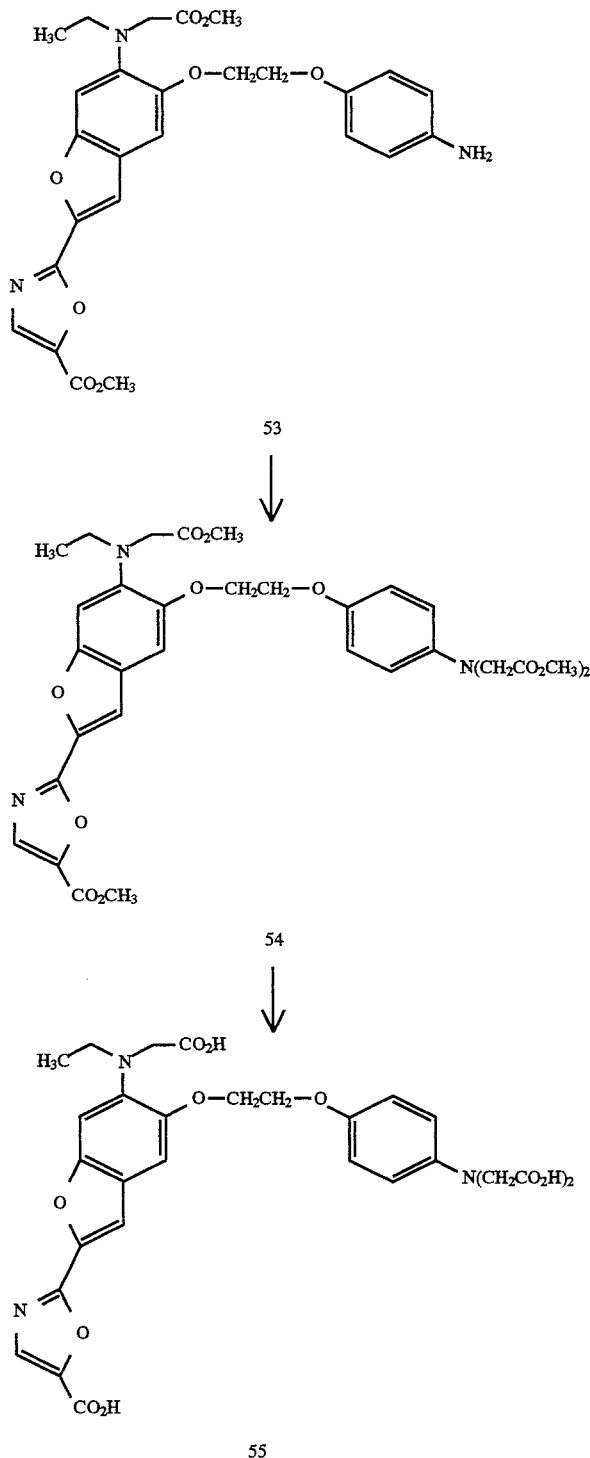

Another indicator, "NEAP-INDO1", can be prepared as summarized below and shown in Scheme 6. Starting with the o-benzyloxy aniline (56), N-ethyl-2-hydroxyaniline, (59), can be prepared by either of two routes. The first route is by the direct alkylation of (56) with $NaBH_4$/acetic acid. The second route includes first synthesizing the intermediate N-acetyl-2-benzyloxyaniline (57) from (56) by reaction of the latter with acetic anhydride/pyridine. Intermediate (57) can then be reduced to the N-ethyl benzoate derivative (58) by lithium aluminum hydride. Hydrogenolysis (Pd/C,$H_2$) of (58) yields the target (59). This amino phenol is then alkylated at the amino nitrogen and phenolic oxygen with methylbromoacetate to give (60), which can be further elaborated to yield the NEAP-INDO1 methyl ester (61) and free acid (62) using published procedures (Grynkiewicz et al., *J. Biol. Chem.* 260, 3440–3450; 1985).

Scheme 6

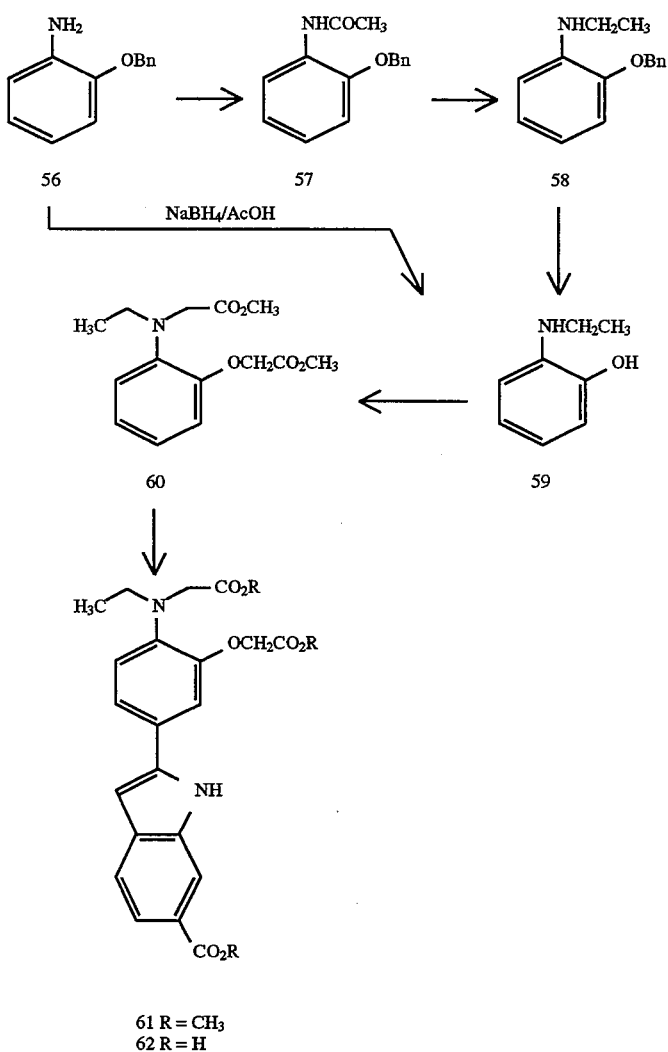

61 R = CH₃
62 R = H

The related indicator, "NEAP-INDO2", can be prepared as shown in Scheme 7. Hydrogenolysis of (58) with Pd/C and $H_2$ yielded the free phenol (63), coupling of which to (46) yields (64). Reduction of this N-acetyl derivative (lithium aluminum. hydride) gives (65) with the N-ethyl function. Subsequent alkylation with methyl bromoacetate produces (66). Introduction of the indole substituent can be achieved by the published method of Grynkiewicz et al. (*J. Biol. Chem.* 260, 3440–3450; 1985) to give (67). Reduction of the nitro substituent in (67) (Pd/C or Pt/C,$H_2$) gave (68). Dialkylation (methyl bromoacetate) of the resulting aniline derivative produces (69). Saponification (NaOH, methanol; $H^+$) provides the indicator NEAP-INDO2 (70).

Scheme 7
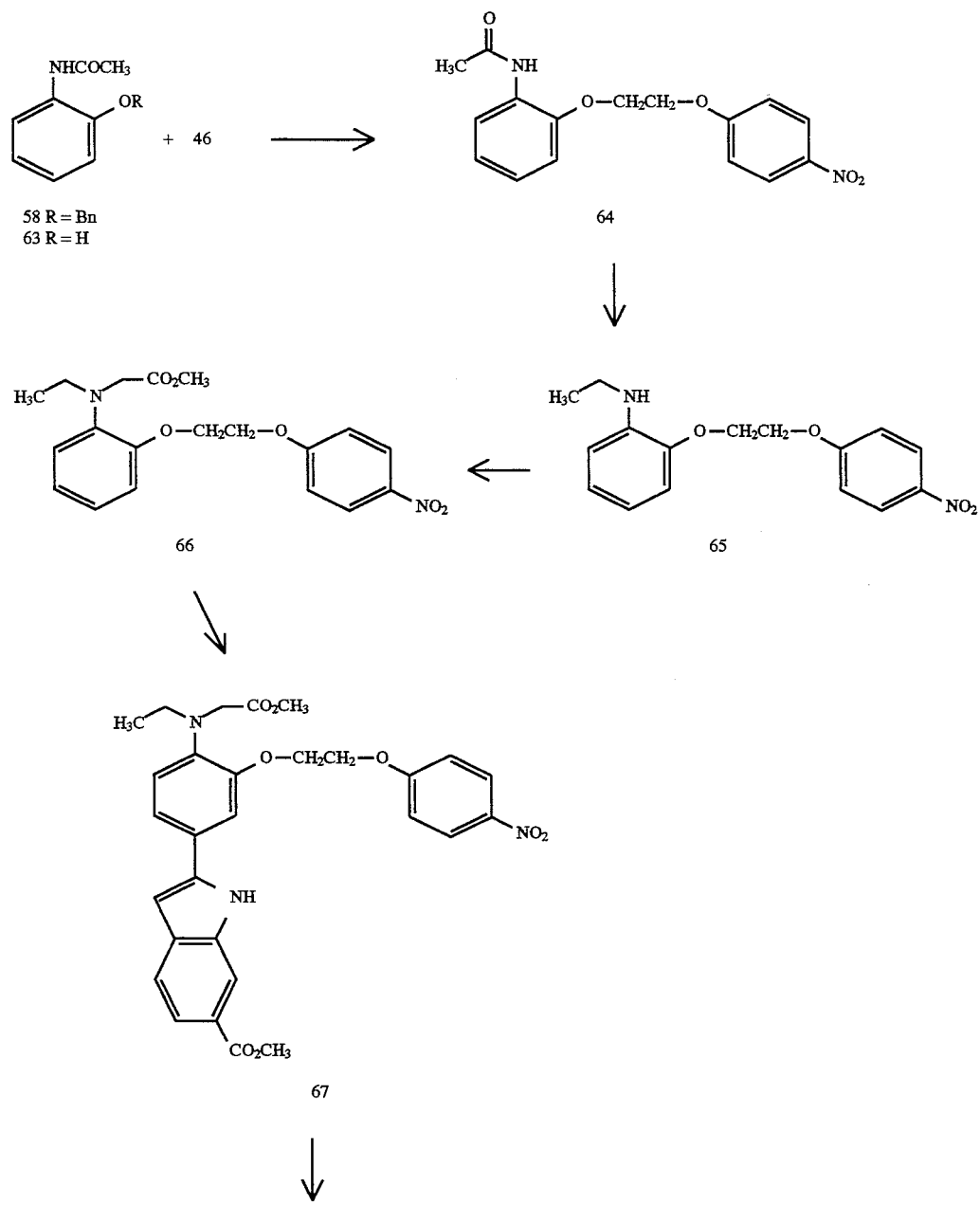

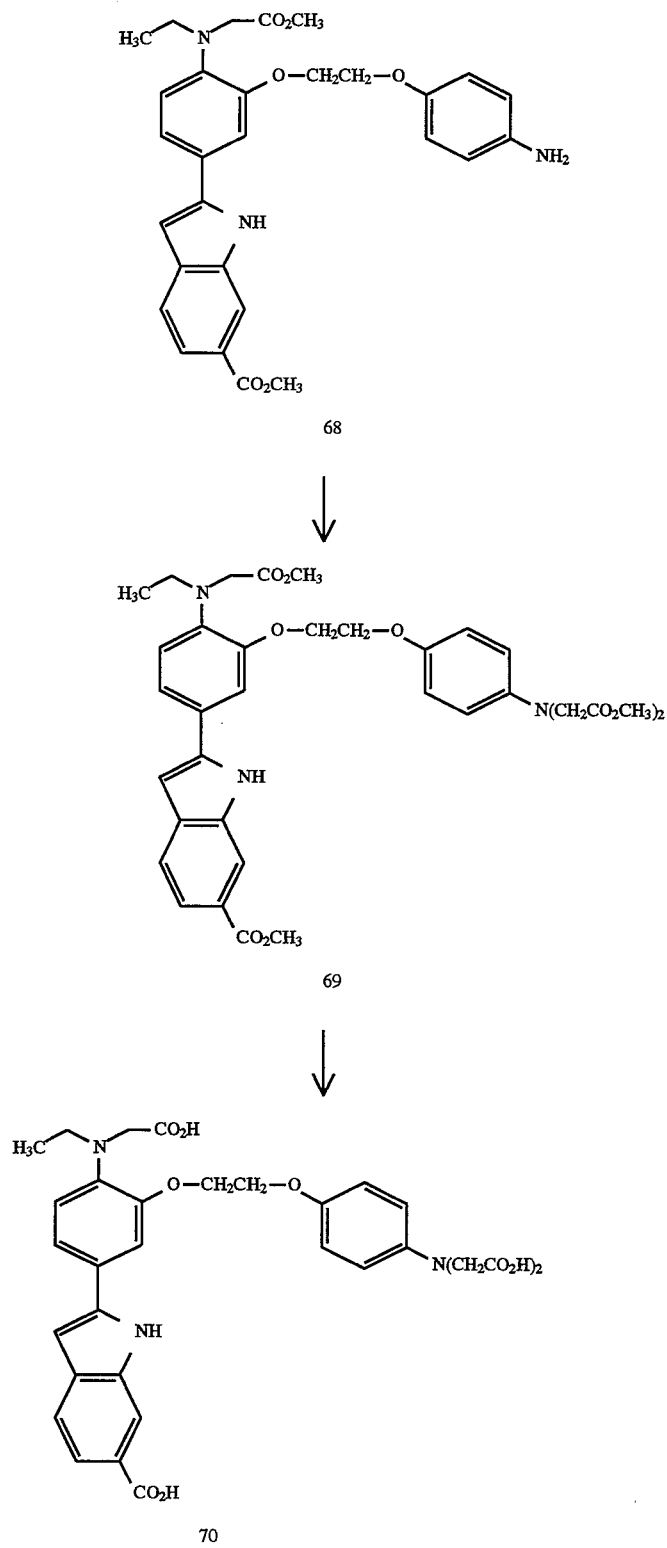
The indicators of Formula V can be prepared as shown and described below. The indicators, "NEAP-FLUORHO1", can be prepared as shown below in Scheme 8.

Scheme 8

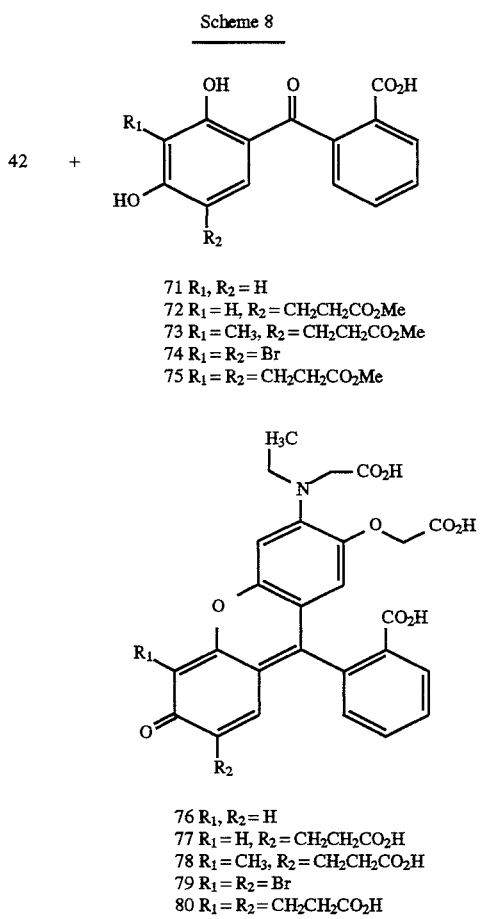

71 R₁, R₂ = H
72 R₁ = H, R₂ = CH₂CH₂CO₂Me
73 R₁ = CH₃, R₂ = CH₂CH₂CO₂Me
74 R₁ = R₂ = Br
75 R₁ = R₂ = CH₂CH₂CO₂Me

76 R₁, R₂ = H
77 R₁ = H, R₂ = CH₂CH₂CO₂H
78 R₁ = CH₃, R₂ = CH₂CH₂CO₂H
79 R₁ = R₂ = Br
80 R₁ = R₂ = CH₂CH₂CO₂H

Compound (42), prepared as described above for the synthesis of "NEAP-FURA", can be treated with $ZnCl_2$ in tetrahydrofuran (THF) in the presence of one of a series of substituted benzophenones (71)–(75). This synthetic scheme is analogous to that followed for the synthesis of calcium chelators by Smith et al. (*Chem. Soc. Perkin Trans.* 2, 1195–1204; 1993).

The "NEAP-FLUORHO2" series can be prepared as illustrated in Scheme 9 by condensing the N-ethyl compound (50) with the benzophenone derivatives (71)–(75) to yield the ester form of NEAP-FLUOROHO2 derivatives (81)–(85). The ester groups can then be hydrolyzed (NaOH/aqueous methoanol; $H^+$) to give the series of NEAP-FLUORHO indicators shown (86)–(90). This synthesis is analogous to the procedure of Smith, et al. and uses the approach outlined above for NEAP-3. These analogs are expected to have greater quantum efficiencies and, due to the higher charge, a reduced tendency to leak from cells.

Scheme 9

50 + 71–75

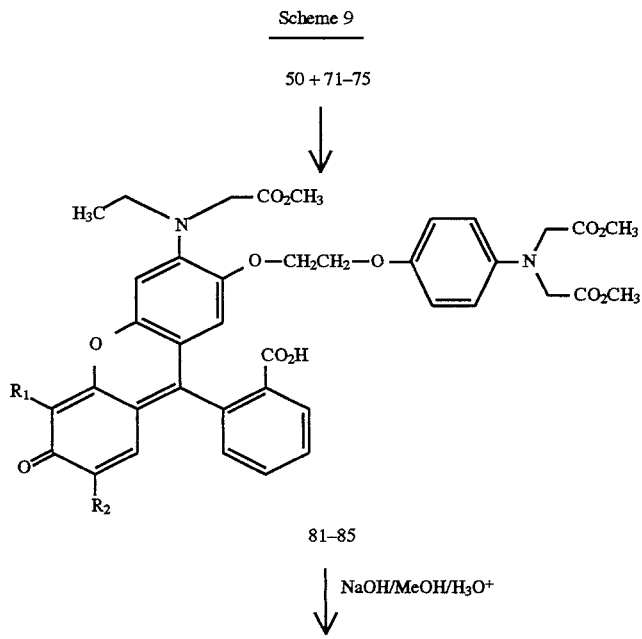

81–85

NaOH/MeOH/$H_3O^+$

-continued
Scheme 9

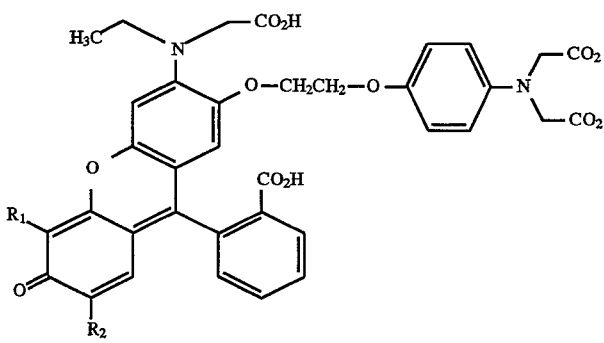

86–90

Finally, the "NAAP-Red" series of indicators, as represented by Formula VI, may be formed using known methods and available reagents, including those described for analogous compounds of the present invention, e.g., Formula III.

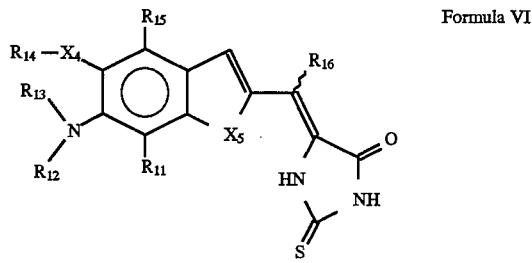

Formula VI

IV. Measurement of Intracellular pH

The present invention also includes methods of determining intracellular pH and intraorganelle pH, wherein a compound of the invention is introduced into a cell and the spectrum of the compound is recorded. The features of the recorded spectrum are compared with the spectral features of the compound at known pH, and the intracellular pH is then calculated.

A. Loading

The compounds of the instant invention can be introduced into the cells using techniques known in the art. Typically, the indicators are loaded into the cytosol in a cell permeant, acetoxymethyl ester form (see, e.g., Tsien et al., Nature 295, 68 (1982); Tsien et al., J. Cell Biol. 94, 925, (1982)). In brief, the cells are incubated with the acetoxymethyl ester of the chosen indicator and then washed to remove unloaded indicator. Loading efficiency is typically in the range of about 10–30%. The fluorinated NMR indicators are used at a final intracellular concentration of about 0.1–1.0 mM, while the fluorescent indicators can be used at somewhat lower concentrations, typically about 10–100 µM. In some embodiments, the indicator will be microinjected into the cells. See, e.g., Cobbold and Rink, Biochem. J. 248, 313–328 (1987). In such embodiments, the charged indicator is used rather than the ester form of the indicator.

B. Measurement Techniques

After the cells have been loaded with an indicator of the present invention, the intracellular pH can be determined. The method chosen will, of course, vary with the indicator used and the nature of the system under study. Preferred measurement techniques include $^{19}F$ NMR spectroscopy, flow cytometry, and quantitative fluorescence techniques. The latter can be used on suspensions of cells in a conventional fluorometer, on individual cells using fluorescence microscopy techniques, or on individual cells as a basis for sorting with flow cytometry. However, one of skill in the art will appreciate that any other technique which is capable of detecting at least one physical property which is dependent on whether the intracellular indicator is in the protonated or nonprotonated form can be utilized with the indicators of the present invention to measure intracellular pH. Any analytical technique capable of detecting these effects can be used in conjunction with the pH indicators of the present invention.

i) $^{19}F$ NMR Spectroscopy

According to the present invention, intracellular pH can be determined using $^{19}F$ NMR spectroscopy of cells containing a compound of Formula I or II. Measurements have been carried out on several physiological systems of interest, including, for example, human erythrocytes and perfused rat heart. The $^{19}F$ NMR shifts of 5F NEAP-1, 5F NEAP-2, or 5F NEAP-3 provide information which is directly interpretable in terms of the cytosolic pH. These measurements can be made using any standard pulsed NMR spectrometer equipped with a fluorine NMR probe. Typically, at least 100 transients are required for the measurements.

Without being bound to any particular theory of operation, it is known that intracellular fluorine resonances exhibit a small downfield chemical shift, typically 0.1–0.3 ppm (see, e.g., London and Gabel, Biochemistry 28, 2378–2382 (1989)). The magnitude of this shift, however, is insignificant in comparison to the 11 ppm titration shift of the indicator. In any event, the magnitude of this shift may be determined and corrected. In alternate embodiments, for an indicator such as NEAP-3 which contain a second fluorine to serve as a chemical shift reference both fluorines will experience a similar intracellular shift, making correction unnecessary. There is also exchange broadening of the resonance, which becomes more significant at higher magnetic field strengths. In general, the degree of broadening depends on the dissociation rate constant of the proton from the indicator. This rate is dependent on the particular indicator, on the temperature, and on the composition of the solution in which the indicator is placed. Buffers, some of which exist naturally in the cell, catalyze the exchange of protons on and off the indicator, and hence lead to narrowing of the resonance. If the exchange is sufficiently rapid on the NMR time scale, i.e., the dissociation rate constant of the protonated indicator $k_{-1} \gg \pi\Delta v/\sqrt{2}$, where $\Delta v$ is the chemical shift difference of the resonance under study between the protonated and unprotonated forms of the indicator, then the observed chemical shift can be used to determine the intracellular pH according to the relation:

$$pH = pK - \log\left(\frac{\delta_O - \delta_U}{\delta_P - \delta_O}\right)$$

where pK is the pK of the indicator, $\delta_o$ is the observed chemical shift, and $\delta_U$ and $\delta_P$ are the shifts of the unprotonated and fully protonated forms of the indicator, respectively. Although the above equation is expected to be generally adequate, at very high fields and low temperatures, the exchange might become slow enough to require a correction, as described, for example, in London, *J. Magn. Reson. Series A* 104, 190–196 (1993).

Figure 2:
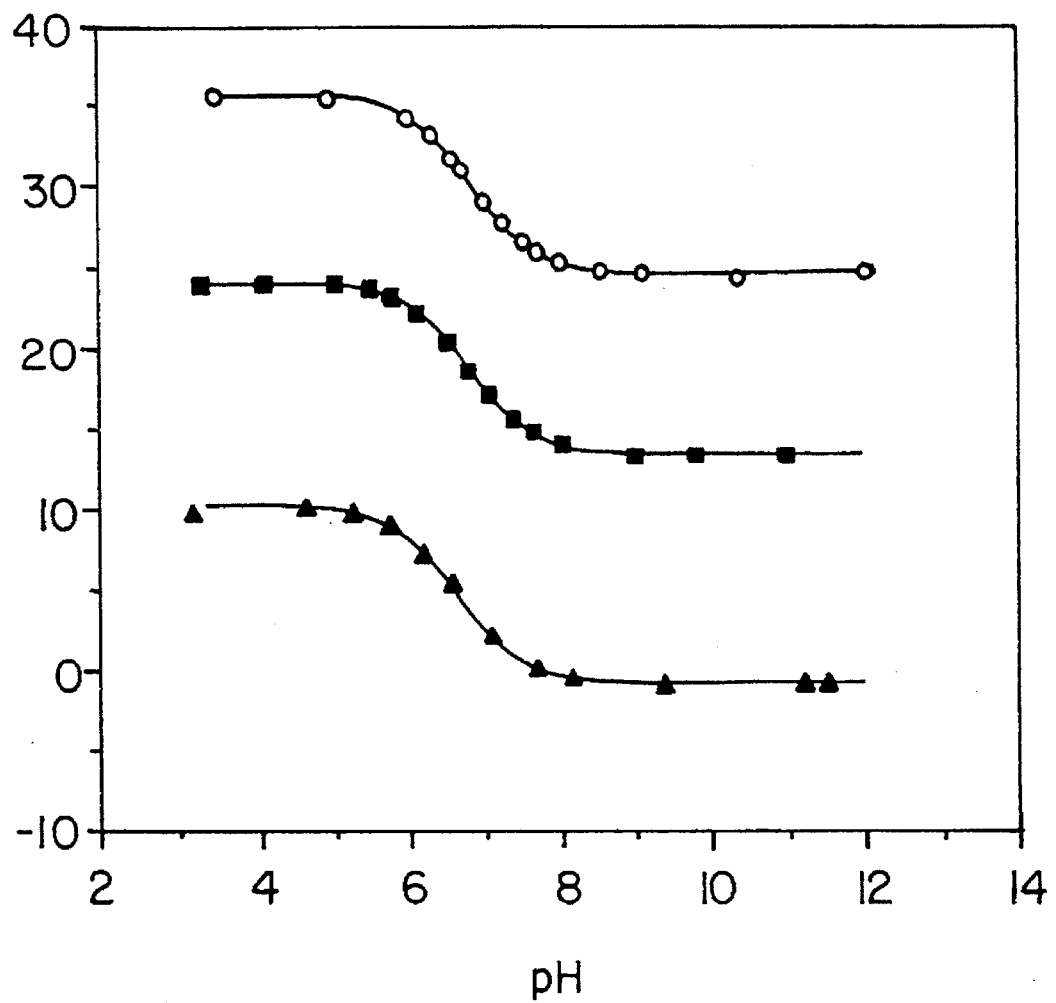
FIG. 2 shows fluorine-19 spectrum shifts as a function of pH for 5F NEAP-1 (○), 5F NEAP-2 (▲), and 5F NEAP-3 (■). The shift for 5F NEAP-1 is referenced to the tetrafluorophthalate $^{19}$F resonance, while the data for 5F NEAP-2 and 5F NEAP-3 correspond to the shift differences between the two fluorine resonances. The theoretical curves correspond to: $\delta_1$=35.6 ppm, $\delta_2$ 24.7 ppm, pK=6.85 for 5F NEAP-1; $\delta_1$=10.3 ppm, $\delta_2$=–0.8 ppm, pK=6.6 for 5F NEAP-2; and $\delta_1$=24.1, $\delta_2$=13.4, pK=6.8 for 5F NEAP-3.

As an example, a series of $^{19}F$ NMR spectra obtained for the compound 5F NEAP-3 is shown in FIG. 1. As is apparent from this Figure, one of the fluorine resonances is pH sensitive, and the second is almost completely pH insensitive, so that the shift difference between the two resonances can be used to determine the pH using the above expression. The pH titration curves for 5F NEAP-1, 5F NEAP-2 and 5F NEAP-3 are shown in FIG. 2.

ii) Flow cytometry pH may be detected using one of the indicators of Formulas III–VI of the present invention and a fluorescence activated cell sorter (FACS) (e.g., FACStarPLUS, available from Becton-Dickenson, Franklin Lakes, N.J.) with either a single, or more typically, a dual laser configuration, to monitor the fluorescence of the intracellular indicator. According to this technique, a suspension of fluorescent indicator-loaded cells is transferred to a FACS, where a narrow stream of solution containing the cells passes through two laser beams that excite the fluorescent indicator. Photomultipliers amplify the emissions from the indicator, and a computer determines the magnitude of the fluorescence of each cell as it passes through the laser beam. Cells can then be sorted based on the fluorescent spectrum which is in turn dependent on the intracellular pH. The computer may also direct the stream to be electrically charged depending on which cells are to be collected. The stream is then broken into droplets by an ultrasonic transducer so that each droplet contains a single cell. If the drop is not charged, it passes straight through a magnetic field and is discarded. If the drop is electrically charged, it will be deflected by a magnetic field and collected in a collection tube. Thus, the use of FACS in combination with the fluorescent indicator allows sorting cells based on the intracellular pH.

Generally, for use with the fluorescent indicators of the instant invention, the FACS should be equipped with a 560 nm short pass interference filter, and 405 nm and 485 nm filters for monitoring the indicator. Logarithmic and linear integrated signals generated from the stream-laser intersection can be collected and organized in the form of 256-channel single-parameter histograms. Scatter-gated viable cells ($1\times10^4$) are analyzed, and the resulting histograms provide information regarding the percentage reactivity, peak channel location, and relative fluorescence intensity.

iii) Quantitative Fluorescence Techniques

According to some embodiments of the present invention, the indicators of Formula III–VI, when protonated, will emit or excite light at a wavelength different from the wavelength which they emit or excite when unprotonated, or exhibit a quantum efficiency which is dependent on the degree of protonation of the indicator. Thus, pH can also be determined using the indicators of Formula III–VI in conjunction with quantitative fluorescence techniques, for example, dual wavelength excitation or emission techniques and the ratio method (see Tsien et al., *Cell Calcium* 6, 145–157 (1985)).

Fluorescent embodiments of the present invention can be used to determine intracellular pH. Generally, the pH can be determined from the measured fluorescence intensity using the relation:

$$pH = pK - \log\left(\frac{F_O - F_U}{F_P - F_O}\right)$$

where $F_O$ is the observed fluorescence, and $F_P$ and $F_U$ are the fluorescence intensities of the protonated and unprotonated indicator, respectively.

Alternatively, where the fluorescent indicator undergoes a fluorescence emission shift or excitation shift, the pH can be determined using the ratio method in a manner analogous to the determination of cytosolic calcium ion concentration with the calcium ion indicators Fura-2 or Indo-1. (See, e.g., Grynkiewicz) A fluorescence ratio measurement which compares the excitation or the emission spectrum obtained at two wavelengths, $\lambda_1$ and $\lambda_2$ can be used to determine pH. This has the advantage that the ratio so obtained is independent of the indicator concentration, and so is more useful for imaging applications. In this case, the choice of $\lambda_1$ and $\lambda_2$ is not exactly determined, but in general these are chosen near the maximum in the emission or excitation spectrum for the unprotonated and for the protonated forms of the indicator. The pH can then be determined from the relation:

$$pH = pK - \log\left(\frac{R_O - R_{Min}}{R_{Max} - R_O} \times \frac{S_{U2}}{S_{P2}}\right)$$

where $S_{U2}$ and $S_{P2}$ are the fluorescence signals of unprotonated indicator and protonated indicator at a particular wavelength, $\lambda_2$, respectively, R is the fluorescence ratio obtained at two excitation or emission wavelengths, $\lambda_1$ and $\lambda_2$, $R_{Min}$ is the minimum value of this ratio obtained at low pH, and $R_{Max}$ is the maximum ratio obtained at high pH. Using the fluorescent indicators, pH values can be determined on populations of cells suspended in cuvettes, or in individual cells using dual wavelength excitation or emission techniques and the ratio method discussed above.

C. Diagnosis of Disease

In another aspect, the present invention provides methods and materials for the diagnosis of diseases which are characterized at least in part by changes in the intracellular pH of at least one cell type. Such diseases include, e.g., diseases which alter the normal cellular glycolytic flux thereby disturbing the pH homeostasis and or the pH response to stress, and McArdle's disease, which is characterized by the failure of the skeletal muscle cells to process glycogen (Ross et al., *N. Engl. J. Med.* 304, 1338–1342; 1981; Lewis et al., *J. Appl. Physiol.* 59, 1991–1994; 1985). Cancerous cells, including solid tumor cells, have been shown to experience intracellular acidification, ostensibly as a result of reduced blood flow. Murine RIF-1 tumor cells are also noted for their dramatic intracellular acidification in response to hyperglycemia (see, e.g., Goldberg, et al., *Clin. Chem.* 39.2360–2374; 1993; Weinhouse, et al., *Krebsforsch.* 87, 115–126; 1976; Evelhoch et al., *PNAS USA* 81: 6496–6500; 1984).

According to the method of the invention, a disease in a mammal, which disease is characterized at least in part by changes in intracellular pH of at least one cell type, is diagnosed by (1) introducing a compound of the invention to cells suspected of being in a diseased state, (2) recording the fluorescence or $^{19}F$ NMR spectrum of the cells, (3) determining the pH of the cells, and (4) comparing the pH of the cells with the pH of healthy cells to determine the presence of the disease.

Introduction of the compound to the cells may be performed in one of several ways. The cells of interest may be isolated by the collection of bodily fluids believed to contain diseased cells, such as blood, saliva, urine, semen, mucose and the like, using common techniques for sample collection and storage such as described in THE MERCK MANUAL 16th Ed. (Merck & Co. 1992), which is incorporated herein by reference. Cells may also be obtained by the biopsy of tissues believed to contain diseased cells using standard surgical procedures. Following the collection of the sample, the cells of interest may be isolated using stardard techniques. The pH of the isolated cells, or organelles therein, can then be determined as described above. Alternatively, the sample itself may be exposed to an ester of a compound of the invention.

Once the esterifed compound enters a cell, hydrolysis of the ester functionality within the cell will result in a carboxylate anion that will not cross the cell membrane. Also, an ester of a compound of the invention may also be introduced to the mammal directly by such techniques as injection or topical delivery. Again, the esterified compounds will migrate into the cells of interest, whereupon hydrolysis to the caboxylate will prevent their escape from the cell. Various topical and injectable formulations may be made using standard methods and materials such as described in REMINGTON'S PHARMACEUTICAL SCIENCES (Mack Publishing Co. 1989), which is incorporated herein by reference. The NEAP derivatives described herein are preferred compounds for such applications.

Once the indicator has been introduced to the cells to be examined, the pH of the cells is determined using the techniques described above. The cellular pH is then compared against the range of pH values assoicated with healthy cells of the same type. A pH out of the range associated with healthy cells would be an indication of a disease state. It will be appreciated that the methods described herein may also be applied to samples of healthy cells to provide a basis for comparison.

D. Indicator Kits

The present invention also provides kits containing the indicators of the present invention. The indicators may be provided substantially as described herein. Preferably these kits provide the indicators of the present invention in an acetoxymethyl ester form, ready for loading. The kits of the present invention may optionally include a reference standard, either separate or combined with the indicator. Finally, the kits may provide the indicators of the present invention in solid form or in solution, e.g., buffered solution, or DMSO for topical application of indicators to cells.

EXAMPLES

In order that the invention described herein can be more fully understood, the following examples are set forth. It should be understood that these examples are for illustrative purposes only, and are not to be construed as limiting this invention in any manner.

I. General

Starting materials not described herein are available commercially, are known, or can be prepared by methods known in the art.

In the process described herein for the preparation of compounds of this invention, the requirements for protecting groups are generally well recognized by one skilled in the art of organic chemistry. Accordingly, the use of appropriate protecting groups is necessarily implied by the processes contained herein, although not expressly illustrated.

Isolation and purification of the compounds and intermediates described herein can be effected, if desired, by any suitable separation or purification procedure such as, for example, filtration, extraction, crystallization, column chromatography, thin-layer chromatography or thick-layer chromatography, high-pressure liquid chromatography, or a combination of these procedures. Specific illustrations of suitable separation and isolation procedures are described in the examples herein. However, other equivalent separation or isolation procedures can, of course, also be used.

II. Synthesis

Unless otherwise noted, commercially available reagents and dry solvents were used as received. Reactions were carried out under an atmosphere of argon and reaction temperatures refer to the bath. Unless stated otherwise, all reported compounds were homogeneous as judged by the thin layer chromatography (TLC) analysis and their NMR spectra. Flash column chromatography (FCC) was performed with Merck Silica Gel 60 (40–63 µm). Synthetic intermediates were characterized using $^1$H nuclear magnetic resonance ($^1$H NMR) and $^{19}$F nuclear magnetic resonance ($^{19}$F NMR). Proton Sponge is 1,8-bis(dimethylamino) naphthalene.

$^1$H nuclear magnetic resonance ($^1$H NMR) and $^{19}$F nuclear magnetic resonance ($^{19}$F NMR) were measured at 500 MHz and 470 MHz, respectively, on a General Electric GN-500 spectrometer. Unless otherwise note, NMR spectra were obtained in CDCl$_3$ solution. For $^1$H NMR, the residual CHCl$_3$ in CDCl$_3$ was employed as the internal standard and assigned as 7.26 ppm downfield (d) from tetramethylsilane (TMS). For $^{19}$F NMR, hexafluorobenzene was employed as the internal standard and assigned as 0.0 parts-per-million (ppm). Melting points were determined on a Fisher-Johns melting point apparatus and are uncorrected.

N-Ethyl-2-benzyloxy-4-fluoroaniline (2)

Two pellets of sodium borohydride (NaBH$_4$, 311 mg) were added to a solution of 3.18 g (14.7 mmol) of 2-benzyloxy-4-fluoroaniline in 80 ml of glacial acetic acid. Another two pellets (320 mg) were added 0.5 hours after the first addition. The reaction mixture was then stirred overnight at room temperature. The reaction mixture was neutralized with 3N sodium hydroxide (NaOH) solution, extracted with ether, and the combined extracts washed with H$_2$O and dried over magnesium sulfate (MgSO$^4$). Removal of the solvent yielded 3.06 g of crude product. Flash chromatography (9:1 hexane/ethyl acetate) of this material yeilded 1.22 g (35%) of white crystals, m.p. 58°–59°. $^1$H NMR : 1.24(t, J=7.1 Hz, 3H), 3.12(q, J=7.1, 2H), 5.03(s, 2H), 6.5(m, 1H), 6.6 (m, 2H), 7.4(m, 5H).

N-Ethyl-2-hydroxy-4-fluoroaniline (3)

A solution of 847 mg (3.46 mmol) of 2 in 30 ml of ethyl acetate was hydrogenolyzed, using 109 mg of 10% palladium/carbon catalyst (Pd/C). The reaction proceeded rapidly until one equivalent of hydrogen had been taken up. The catalyst was then filtered through a pad of Celite and the solvent removed to yield 484 mg of product (90%), m.p. 92°–97° C. with decomposition. This material was homogeneous by TLC, R$_f$=0.2 (9:1 hexane/ethylacetate) but discolored rapidly. $^1$H NMR: 1.22 (t, J=7 Hz, 3H), 3.07 (q, J=7 Hz, 2H), 6.5 (m, 2H), 6.7 (m, 1H).

N-Ethyl-2-hydroxy-4-fluoroaniline N,O diacetic acid dibenzyl ester (4)

A mixture of 475 mg (3.06 mmol) of 3, 1.60 g Proton Sponge, 1.74 g benzyl bromoacetate and 20 ml of acetonitrile was heated at reflux for 48 hours under an argon atmosphere. The cool solution was filtered and ether was then added to the filtrate. The resulting precipitate was filtered off and the filtrate washed with pH 2 buffer, saturated NaCl solution, water and dried (MgSO$_4$). After removal of the solvent, the resulting crude product was purified by flash chromatography (85:15 hexane/ethyl acetate) to yield 303 mg (23%) of clear colorless oil. $^1$H NMR : 1.05 (t J=7.1 Hz, 3H), 3.27 (q J=7.1 Hz, 2H), 4.03 (s, 2H), 4.67 (s, 2H), 5.05 (s, 2H), 5.17 (s, 2H), 6.47 (dd J=2.7 and 9.8 Hz 1H), 6.60 (ddd J=8.3 and 2.4 Hz, 1H).

N-Ethyl-2-hydroxy-4-fluoroaniline N,O diacetic acid (5)

Hydrogenolysis of the diester 4 (54 mg, 0.1 mmol) in 15 ml of ethyl acetate with 10 mg, 10% Pd/C, yielded the free acid, 27 mg, m.p. 54°–56° C., $^1$H NMR (D$_2$O): 0.99 (t J=7 Hz, 3H), 3.23 (q J=7 Hz, 2H), 3.89 (br s, 2H), 4.64 (br s, 2H) 6.7 (m, 2H), 7.1 (m, 1H), $^{19}$F NMR (D$_2$O): 43.03 (m).

Methyl-3-fluoro-4-bromomethyl benzoate (6)

A mixture of 7.32 g (43.6 mmol) methyl-3-fluoro-4-methylbenzoate, 4.92 g N-bromosuccinimide (NBS) and a few mg of 2,2-azobisisobutyronitrile (AIBN) in 80 ml of carbontetrachloride (CCl$_4$) were brought to reflux and illuminated with a high intensity lamp. The reaction was rapid and within 2 hours, all of the NBS has been converted to succinimide. TLC and NMR analysis indicated a 1:1 mixture of product and starting material as judged by the appearance of a new signal at 4.49 corresponding to bromination of the methyl group. The mixture was worked up by filtering the succinimide and washing the CCl$_4$ solution, first with aqueous sodium sulfate (Na$_2$S$_2$O$_3$) and then with aqueous sodium bicarbonate (NaHCO$_3$). The product obtained after drying and removal of the solvent was recycled with additional NBS and treated as above to yield 7.46 g of yellow oil which was an 8:1 mixture of product and starting material and was used as such in the next step.

2-(2-Fluoro-4-methoxycarbonylbenzyloxy)-4-fluoronitrobenzene. (7)

A mixture of 7.37 g of the previously described impure 6, 30 ml dimethylformamide (DMF), 4.5 g potassium carbonate K$_2$CO$_3$ and 4.29 g (30 mmol) of 2-nitro-5-fluorophenol was heated at 70° C. in an oil bath. After two hours, the reaction mixture was cooled and poured into ice water and the product filtered off. The crude product was extracted with warm hexane to remove the methyl-3-fluoro-4-methylbenzoate impurity carried along from the preparation of (6). The resulting cream colored product, 5.74 g, after recrystallization from ethyl acetate had m.p. 163°–165° C. $^1$H NMR: 3.92 (s, 3H), 5.29 (s, 2H), 6.78 (m, 1H), 6.86 (dd J=3.4 and 9.5 Hz, xH), 7.75 (m, 2H), 7.89 (dd J=1 and 6.4 Hz, 1H), 8.00 (dd J=6.9 and 9.1 Hz, 1H).

2-(2-Fluoro-4-methoxycarbonylbenzyloxy)-4-fluoroaniline. (8)

A solution of 1.28 g (3.96 mmol) of 7 in 25 ml ethyl acetate and 125 mg of 5% Pt/C was reduced with hydrogen at atmospheric pressure. After the uptake of 3 equivalents of hydrogen the catalyst was filtered off and the solvent removed to yield 1.14 g (98%) of product, m.p. 92°–95° C. $^1$H NMR: 3.92 (s, 3H), 5.16 (s, 2H), 6.54 (ddd J=2.5, 5.9 and 5.9 Hz 1H) 6.65 (m, 2H), 7.55 (dd J=7.5 and 7.5 Hz, 1H) 7.74 (dd J=1.2 and 10.3 Hz, 1H), 7.83 (dd J=1.2 and 8 Hz, 1H).

N-Ethyl-2(2-fluoro-4-methoxycarbonylbenzyloxy)-4-fluoroaniline (9)

To a solution of 850 mg (2.90 mmol) of 8 in 17 ml of glacial acetic acid were added 4 pellets (600 mg) of NaBH$_4$ over a period of 2 hours. TLC indicated the slow appearance of a produce at R$_f$=0.8 (7:3 hexane/ethyl acetate). Stirring at room temperature was continued for a total of 6 hours. The reaction was neutralized with aqueous NaHCO$_3$. The product precipitated and after filtration was obtained as buff colored crystals (654 mg, 70%) and after recrystillaziation from hexane had m.p. 109°–111° C., $^1$H HMR (CDCl$_3$): 1.25 (t, J=7.1 Hz 3H), 3.11 (q, J=7.1 Hz, 2H), 3.92 (s, 3H), 5.15 (s, 2H), 6.5 (m, 1H), 6.6 (m, 2H), 7.5 (dd J=7.5 and 7.5 Hz, 1H), 7.75 (br d J=10 Hz), 7.84 (br x, J=7.5 Hz, 1H).

N-Ethyl-2(2-fluoro-4-methoxycarbonylbenzyloxy)-4-fluoro aniline, N-acetic acid, methyl ester (10)

A mixture of 624 mg (1.94 mmol) of 9, 465 mg Proton Sponge, 360 mg methyl bromoacetate and 10 ml of dry acetonitrite was refluxed under argon for 54 hours. After 24 hours of reflux, an additional 65 mg each of methyl bromoacetate and Proton Sponge was added. The cool solution was diluted with ether and the amine salt filtered off. The filtrate was washed with pH buffer, water and dried (MgSO$_4$). Removal of the solvent yielded 670 mg of crude product which after flash chromatography (85:15 hexane/ethyl acetate) yielded 419 mg (55%) of crystalline product, m.p. 61°–62° C. $^1$H NMR (CDCl$_3$) 1.07 (t J=7 Hz, 3H), 3.26 (q J=7 Hz, 2H), 3.58 (s, 2H), 3.91 (s, 3H), 3.94 (s, 3H), 5.16 (s, 2H), 6.1 (m, 2H), 7.01 (dd J=2 and 6 Hz, 1H), 7.57 (dd J=7.5 Hz, 1H), 7.73 (dd J=1 and 10 Hz, xH) , 7.84 (dd J=1 and 7.5, Hz, 1H) , $^{19}$FNMR (DMF-d$_7$), 43.2 (m, 1F), 45.7 (m, 1F).

N-Ethyl-2-(2-fluoro-4-carboxybenzyloxy)-4-fluoroaniline-N-acetic acid (11)

A sample of 10, 42 mg, (0.11 mm) was hydrolyzed with 1M NaOH (3 ml) in aqueous methanol and after acidification (0.6N HCl) yielded 33 mg (84%) pure acid (11), m.p. 73°–77° C.

$^1$H NMR (D$_2$O): 0.61 (t J=7 Hz, 3H), 2.76 (q J=7 Hz), 4.54 (s, 2H), 4.84 (s, 2H), 6.38 (ddd J=7.5, 7.5 and 2.5 Hz, 1H), 6.50-(dd J=10.5 and 2.5 Hz, 1H), 6.70 (dd J=8.5 and 6.5 Hz, 1H), 7.28 (dd J=7.5 and 7.5 Hz, 1H), 7.36 (br d J=10.5 Hz, 1H), 7.44 (br d J=8.5 Hz, 1H); $^{19}$F (DMF-d$_7$): 43.2 (m, 1F), 45.7 (m, 1F).

N-Acetyl-2-benzyloxy-4-fluoroaniline (12)

Acetic anhydride (10 mL) was added to a solution of 2-benzyloxy-5-fluoroaniline (700 mg 3.2 mmol) in pyridine (20 mL) and the reaction mixture was stirred for 1 hr. ice water (10 mL) was added to the mixture and the crude product was filtered and washed with water. Recrystallization from benzene afforded benzyl ether 12 as a white solid (801 mg, 96%), M.P.: 136° C.–138° C. $^1$H NMR (CDCl$_3$): 2.00 (s, 3H), 4.94 (br s, 2H), 6.8–6.7 (m, 2H), 7.2–7.1 (br s, 5H), 8.16 (dd, J=8.6 Hz, 1H).

N-Acetyl-2-hydroxyl-5-fluoroaniline (13)

A mixture of benzyl ether 12 (800 mg. 3.1) in ethyl acetate (15 mL) and Pd/C (100 mg) was stirred overnight under H$_2$ (1 atm). The reaction mixture was filtered through Celite and concentrated under reduced pressure. The crude product was recystallized from ethyl acetate to give phenol 13 as a white solid (512 mg, 98%). MP: 185°–186° C. $^1$H NMR (CDC$_3$): 6.57(dd, J=10.5, 2.5 Hz, 1H), 6.75 (dd, J=9.5, 2.5 Hz, 1H), 6.88 (dd, J=9.5, 5.5 Hz, 1H), 7.35 (br s, 1H), 9.05 (br s, 1H).

1-Bromo-2-(2-fluoro-5-nitrophenoxy)-ethane (14)

Potassium carbonate (2.3 g, 16.7 mmol) was added to a solution of 2-fluoro-4-nitrophenol (1.5 g, 10 mmol) in dimethyl formamide (10 mL) and the mixture was stirred for 10 min. Dibromoethane (2.5 mL, 29 mmol) was added to the reaction mixture and was heated at 90° C. overnight. The reaction mixture was diluted with ether and the ether layer was washed with water, brine and then dried (MgSO$_4$). The solvent was removed under reduced pressure and the crude product was fractionated by FCC with 2.5% ethyl acetate in hexane to yield 14 as a yellow oil (1.9 g, 75%). $^1$H NMR (CDCl$_3$): 3.69 (t, J=6 Hz, 2H), 4.44 (t, J=6 Hz, 2H), 7.03 (dd J=8.5 Hz, 1H), 8.1–7.9 (m, 2H).

1-(2-Acetamido-5-fluorophenoxy)-2-(2-fluoro-4-nitrophenoxy)ethane (15)

A mixture of phenol 13 (450 mg, 2.7 mmol) and bromoethane 14 (850 mg, 3.2 mmol) in dimethyl formamide (10 mL) containing K$_2$CO$_3$ (500 mg, 3.6 mmol) was heated at 70° C. overnight. The reaction mixture was quenched with ice water filtered and washed with cold water. The crude product was fractionated by FCC (dry application with 50% EtOAc/Hexane) to provide 15 as a pale tan solid (1.0 g, 88%). M.P.: 192°–194° C. $^1$H NMR (CDCl$_3$): 2.15 (s, 3H), 4.6–4.4 (m, 2H), 7.59 (br s, 1H), 8.03 (dd, J=10.5, 2.5 Hz, 1H), 8.08 (dd, J=9.5, 2.5 Hz, 1H), 8.29 (dd, J=9.5, 7 Hz, 1H).

1-(2-Acetamido-5-fluorophenoxy)-2-(2-fluoro-4-aminophenoxy)ethane (16)

A mixture of nitro compound 15 (1.0 g, 3.1 mmol) in ethyl acetate (20 mL) and Pt/C (200 mg) was stirred for 2 hrs under H$_2$ (1 atm). The reaction mixture was filtered through Celite and concentrated under reduced pressure. The crude product was recrystalized with benzene providing amino ethane 16 as a white solid (709 mg, 78%), m.p. 134°–136° C. $^1$H NMR (CDCl$_3$): 2.12 (s, 3H), 4.29 (s, 4H) (s, 4H), 6.4–6.3 (m, 1H), 6.46 (dd, J=12.5, 2.5 Hz, 1H), 6.7–6.6 (m, 2H), 6.85 (dd, J=9, 9 Hz, 1H), 8.30 (dd, J=9, 6 Hz, 1H).

1-(2-N-Ethylamino-5-fluorophenoxy)-2-(2-fluoro-4-aminophenoxy)ethane (17)

Lithium aluminum hydride (ca. 50 mg) was added to 16 (500 mg, 1.5 mmol) in THF (15 mL) and the reaction mixture was stirred overnight. The reaction mixture was quenched with MeOH (1 mL) and filtered through Celite. After concentrating under reduced pressure, the crude product was fractionated by FCC with 50% EtOAc in hexane to yield 17 as a white solid (300 mg, 63%) and recovered starting material 16 (100 mg, 20%). After recrystallization from benzene, the product had m.p. 111°–114° C. $^1$H NMR (CDCl$_3$): 1.23 (t, J=7 Hz, 3H), 3.10 (q, J=7 Hz, 2H), 4.4–4.2 (m, 2H), 6.37 (br d, J=8.5 Hz, 1H), 6.5–6.5 (m, 2H), 6.57 (br d, J=9 Hz, 1H), 6.6–6.5 (m, 1H), 6.84 (dd, J=9, 9 Hz, 1H).

1-(N-Ethylamino-5-fluorophenoxy)-2-(2-fluoro-4-aminophenoxy)ethane, N,N',N'-triacetic acid, trimethyl ester (18)

Benzyl bromoacetate (340 mL, 3.6 mmol) was added to the solution of amine 17 (200 mg, 0.6 mmol) and Proton Sponge (660 mg) in acetonitrile CH$_3$CN) (10 mL) and the reaction mixture was heated under reflux for 3 days. The cool reaction mixture was diluted with ether (40 mL) and washed with pH 2 solution (20 mL), water (20 mL), and then brine (20 mL). After drying over MgSO$_4$, the ether solution was concentrated under reduced pressure and fractionated by FCC with 50% EtOAc in Hexane yielding triacetrate 18 as a colorless oil (270 mg, 79%). m.p.: 62°–64° C. $^1$H NMR (CDCl$_3$): 1.87 (t, J=7 Hz, 3H), 3.65 (s, 3H), 3.75 (s, 6H), 4.15 (s, 2H), 4.25 (x, 4H), 4.3–4.2 (m, 2H), 4.4–4.3 (q, J=7 Hz, 2H), 4.5–4.4 (m, 2H), 6.76 (dd, J=9, 2.5 Hz, 1H), 6.85 (dd, J=13.5, 3 Hz, 1H), 7.2–7.1 (m, 2H), 7.46 (dd, J=9, 9 Hz, 1H), 7.83 (dd, J=8.5, 6 Hz, 1H).

1-(N-Ethylamino-5-fluorophenoxy)-2-(2-fluoro-4-aminophenoxy)ethane, N,N',N'-triacetic acid (19)

Potassium hydroxide (50 mg, 0.9 mmol) was added to ester 18 (100 mg, 0.2 mmol) in MeOH (3 mL) and stirred overnight. The reaction mixture was acidified with 1M HCl filtered and washed with water to provide acid 19 as a white solid (73 mg, 80%). M.P.: 110°–115° C., $^1$H NMR (D$_2$O): 0.78 (t, J=7 Hz, 3H), 2.92 (q, J=7 Hz, 2H), 3.68 (br s, 4H), 4.5–4.3 (m, 2H), 4.8–4.6 (m, 2H), 6.08 (br, d,J=8.5 Hz, 1H), 6.20 (d, J=13.5 Hz, 1H), 6.6–6.5 (m, 1H), 6.71 (d, J=9 Hz, 1H), 7.0–6.8 (m, 2H), $^{19}$F (DMSO-d$_6$): 42.4 (m, 1F), 30.3 (m, 1F).

III. pH Measurement in Human Erythrocytes Using $^{19}$F-NMR

Figure 3A:
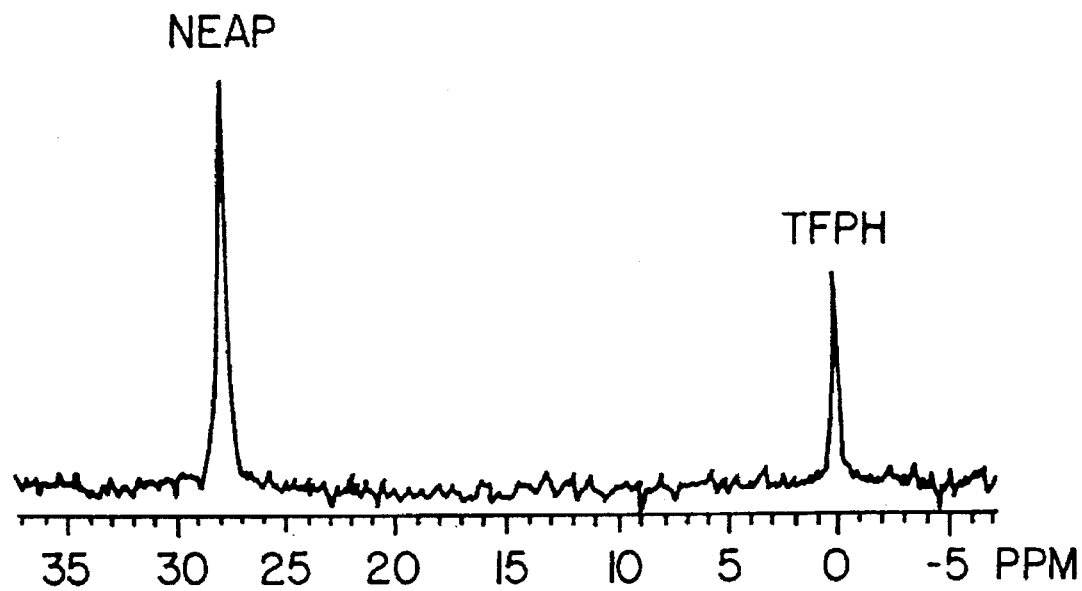
FIGS. 3A and 3B show the $^{19}$F NMR spectra of human erythrocytes loaded with 5F NEAP-1 acetoxymethyl ester suspended in a solution containing 120 mM sodium chloride (NaCl) and 20 mM tris-[N-(2-hydroxyethyl)piperazine-N'-(2-ethanesulfonic acid)] ("tris-HEPES"). Tetrafluorophthalate ("TFPH") is also included as a chemical shift standard.
Figure 3B:
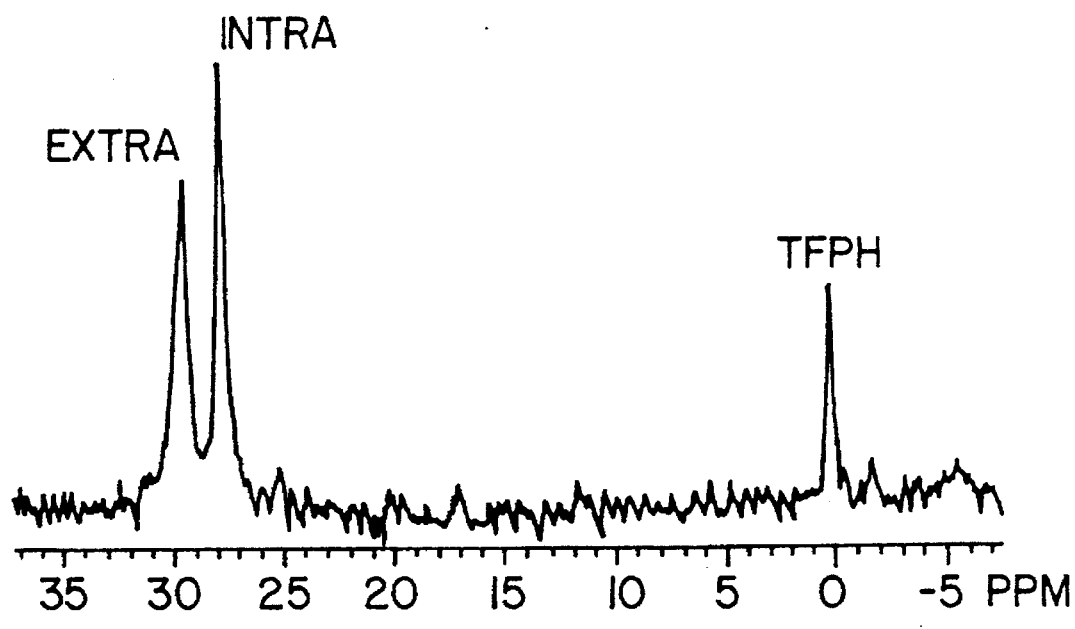

As an illustration of the use of the current invention, the fluorinated indicator 5F NEAP-1 is used to determine the intra- and extracellular pH in a suspension of human erythrocytes. FIG. 3A shows Fluorine-19 NMR spectra from a suspension of human erythrocytes which had previously been loaded for a period of 1 hour with the acetoxymethyl ester form of 5F NEAP-1. A tetrafluorophthalate standard (TFPH) was also added to serve as a chemical shift reference, since 5F NEAP-1 does not have a reference fluorine. Based on the chemical shift difference between the NEAP fluorine resonance and the standard, an intracellular pH value of 7.3 for this preparation is determined. Subsequently, some additional 5F NEAP-1 was added as the free acid. Since this material will not readily cross the cell membrane, it remains extracellular and corresponds to a second resonance which is downfield of the first (FIG. 3B). It is interesting to note that the extracellular resonance is somewhat broader than the intracellular resonance. This results from the more extensive intracellular buffering which accelerates the proton transfer rates on and off the indicator in the intracellular environment relative to the extracellular environment. An extracellular pH value of 7.0 is determined from the shift (this situation is somewhat unusual since in more typical physiological preparations the intracellular pH is lower than the extracellular pH). As noted in the above sections, small errors which result from the intracellular shift displacement of 0.1–0.3 ppm, can be, but have not been accounted for. It is apparent from the spectra that these are small compared with the observed shift effects; however, they can also be included as correction factors. Additionally, it is noted that the 0.3 pH unit difference in chemical shift gives rise to well resolved NMR resonances—illustrating a critical advantage of the series of indicators of the present invention.

Thus, it is seen that the present invention provides new and useful compositions and method for determining intracellular pH. More specifically, the compounds of the invention may be placed within the cell, including the various organelles of the cell to determine the acidity of the local environment. In another aspect, the compounds and methods of the invention may be applied to the diagnosis of diseases which are characterized by changes in the intracellular pH of one or more cell types.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

The disclosures in this application of all articles and references, including patents, are incorporated herein by reference.

What is claimed is:

1. A compound, comprising the formula:

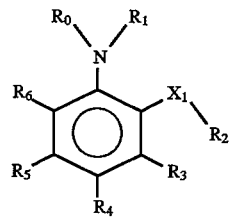

and salts thereof, wherein:

R$_0$–R$_2$ are selected independently from the group consisting of hydrogen, alkyl, aryl, substituted alkyl, substituted aryl, carboxyl, carboxyalkyl, substituted carboxyalkyl, heteroaryl, and substituted heteroaryl;

$R_3$–$R_6$ are selected independently from the group consisting of hydrogen, alkyl, aryl, substituted alkyl, substituted aryl, ether, thioether, substituted amino, halogen, heteroaryl, substituted heteroaryl, carboxyl, carboxyalkyl, substituted carboxyalkyl and amido; and $X_1$ is selected from the group consisting of oxygen, and NH; provided that:

(a) $R_0$, $R_1$ and $R_2$ are not all —$CH_2CO_2H$ or —$CH_2CO_2CH_3$ when $X_1$ is oxygen, $R_4$ is fluorine or hydrogen, $R_5$ is hydrogen, fluorine or methyl, and $R_3$ and $R_6$ are hydrogen;

(b) $R_0$ and $R_1$ are not both —$CH_2CO_2H$ when $X_1$ is oxygen, $R_4$ is fluorine and $R_3$, $R_5$ and $R_6$ are hydrogen, and $R_2$ is —$(CH_2)_2O(CH_2)_2N(CH_2CO_2H)_2$;

(c) $R_0$ and $R_1$ are not both —$CH_2CO_2H$ when $X_1$ is oxygen, $R_3$, $R_4$, $R_5$ and $R_6$ are fluorine or hydrogen, and $R_2$ is —$(CH_2)_2O(C_6H_3N(CH_2CO_2H)_2F)$;

(d) $R_0$ and $R_1$ are not both —$CH_2CO_2H$ or —$CH_2CO_2CH_3$ when $X_1$ is oxygen, $R_4$ is fluorine, $R_5$ is methyl, —$C(CH_3)_2CH_2CO_2H$ or —$C(CH_3)_2CH_2CO_2CH_3$, and $R_3$ and $R_6$ are hydrogen;

(e) $R_0$ and $R_1$ are not both —$CH_2CO_2H$ or —$CH_2CO_2CH_3$ when $X_1$ is oxygen, $R_4$ is fluorine, $R_5$–$R_6$ are hydrogen, and $R_2$ is an (8-amino-2-quinoline)methyl;

(f) $R_0$ and $R_1$ are not both —$CH_2CO_2CH_2C_6H_5$ when $X_1$ is oxygen, $R_4$ is fluorine, $R_3$, $R_5$ and $R_6$ are hydrogen, and $R_2$ is —$(CH_2)_2O(CH_2)_2N(CH_2CO_2CH_2C_6H_5)_2$; and (g) $R_0$ is not —$C(CH_3)_2CO_2CH_3$ or —$C(CH_3)_2CO_2H$ when $R_1$ is hydrogen or methyl, $X_1$ is oxygen, $R_4$ is fluorine, and $R_3$, $R_5$ and $R_6$ are hydrogen; and (h) at least one of $R_3$–$R_6$ is fluorine.

2. The compound of claim 1, wherein $R_0$ is selected from the group consisting of alkyl and substituted alkyl.

3. The compound of claim 2, wherein $R_1$ is selected from the group consisting of carboxyl, carboxyalkyl, and substituted carboxyalkyl.

4. The compound of claim 3, wherein said compound comprises the formula:

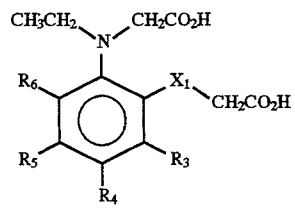

5. The compound of claim 4 wherein $R_3$–$R_6$ are selected independently from the group consisting of hydrogen and fluorine.

6. The compound of claim 5, wherein said compound has the formula:

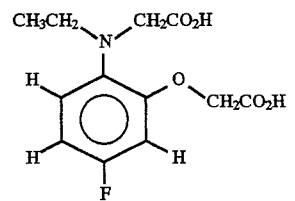

7. The compound of claim 5, wherein said compound has the formula:

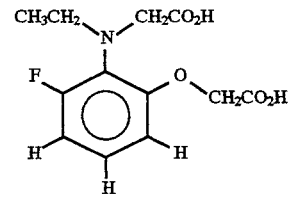

* * * * *